(12) United States Patent
Deransart et al.

(10) Patent No.: US 12,097,129 B2
(45) Date of Patent: Sep. 24, 2024

(54) SHOULDER PATIENT SPECIFIC INSTRUMENT

(71) Applicant: Tornier SAS, Saint Martin (FR)

(72) Inventors: Pierric Deransart, Saint Martin d'uriage (FR); Emmanuel Francois Marie Lizee, Saint Ismier (FR); Delphine Claire Michelle Henry, Saint Ismier (FR); Jean Chaoui, Locmaria-Plouzane (FR); Gilles Walch, Lyons (FR); Pascal Boileau, Nice (FR)

(73) Assignee: TORNIER SAS, Saint Martin (FR)

( * ) Notice: Subject to any disclaimer, the term of this patent is extended or adjusted under 35 U.S.C. 154(b) by 181 days.

(21) Appl. No.: 17/451,499

(22) Filed: Oct. 20, 2021

(65) Prior Publication Data

US 2022/0031475 A1   Feb. 3, 2022

Related U.S. Application Data

(62) Division of application No. 16/521,466, filed on Jul. 24, 2019, now Pat. No. 11,179,249, which is a division of application No. 15/024,747, filed as application No. PCT/IB2014/002711 on Nov. 11, 2014, now Pat. No. 10,405,993.

(Continued)

(51) Int. Cl.
*A61F 2/46* (2006.01)
*A61B 17/17* (2006.01)
*A61B 17/56* (2006.01)
*A61F 2/40* (2006.01)

(52) U.S. Cl.
CPC ........ *A61F 2/4612* (2013.01); *A61B 17/1739* (2013.01); *A61B 17/1778* (2016.11); *A61B 2017/568* (2013.01); *A61F 2/4081* (2013.01); *A61F 2/4603* (2013.01); *A61F 2002/4677* (2013.01)

(58) Field of Classification Search
CPC .................. A61F 2/4612; A61F 2/4081; A61F 2002/4677; A61B 17/1739
See application file for complete search history.

(56) References Cited

U.S. PATENT DOCUMENTS

| | | |
|---|---|---|
| 4,919,670 A | 4/1990 | Dale et al. |
| 5,030,219 A | 7/1991 | Matsen, III et al. |

(Continued)

FOREIGN PATENT DOCUMENTS

| | | |
|---|---|---|
| AU | 2021203700 B2 | 8/2023 |
| CA | 2927086 | 4/2015 |

(Continued)

OTHER PUBLICATIONS

US 9,451,972 B2, 09/2016, Lang et al. (withdrawn)

(Continued)

*Primary Examiner* — Sameh R Boles
(74) *Attorney, Agent, or Firm* — DUANE MORRIS LLP

(57) ABSTRACT

A method of guiding a glenoid prosthesis is disclosed. The method includes preoperatively determining a position and an orientation of a guide feature of a glenoid guide of the present disclosure based on a scapula of a specific patient, and engaging the glenoid guide with the scapula; and inserting a pin having an axis through the guide feature to or through the scapula.

17 Claims, 5 Drawing Sheets

Related U.S. Application Data

(60) Provisional application No. 61/903,814, filed on Nov. 13, 2013.

(56) References Cited

U.S. PATENT DOCUMENTS

| | | |
|---|---|---|
| 5,329,846 A | 7/1994 | Bonutti |
| 5,370,692 A | 12/1994 | Fink et al. |
| 5,383,938 A | 1/1995 | Rohr et al. |
| 5,531,793 A | 7/1996 | Kelman et al. |
| 5,610,966 A | 3/1997 | Martell et al. |
| 5,725,586 A | 3/1998 | Sommerich |
| 5,768,134 A | 6/1998 | Swaelens et al. |
| 5,769,856 A | 6/1998 | Dong et al. |
| 5,779,710 A | 7/1998 | Matsen, III |
| 5,807,437 A | 9/1998 | Sachs et al. |
| 5,824,078 A | 10/1998 | Nelson et al. |
| 5,824,085 A | 10/1998 | Sahay et al. |
| 6,002,859 A | 12/1999 | DiGioia, III et al. |
| 6,129,764 A | 10/2000 | Servidio |
| 6,155,812 A | 12/2000 | Smith et al. |
| 6,172,856 B1 | 1/2001 | Jang |
| 6,183,519 B1 | 2/2001 | Bonnin et al. |
| 6,364,910 B1 | 4/2002 | Shultz et al. |
| 6,385,475 B1 | 5/2002 | Cinquin et al. |
| 6,432,142 B1 | 8/2002 | Kamiya et al. |
| 6,459,948 B1 | 10/2002 | Ateshian et al. |
| 6,648,894 B2 | 11/2003 | Abdelgany et al. |
| 6,699,289 B2 | 3/2004 | Iannotti et al. |
| 6,719,799 B1 | 4/2004 | Kropf |
| 6,772,026 B2 | 8/2004 | Bradbury et al. |
| 6,797,006 B2 | 9/2004 | Hodorek |
| 6,915,150 B2 | 7/2005 | Cinquin et al. |
| 6,944,518 B2 | 9/2005 | Roose |
| 7,468,075 B2 | 12/2008 | Lang et al. |
| 7,469,474 B2 | 12/2008 | Farrar |
| 7,534,263 B2 | 5/2009 | Burdulis, Jr. et al. |
| 7,542,791 B2 | 6/2009 | Mire et al. |
| 7,599,539 B2 | 10/2009 | Kunz et al. |
| 7,618,451 B2 | 11/2009 | Berez et al. |
| 7,634,119 B2 | 12/2009 | Tsougarakis et al. |
| 7,648,530 B2 | 1/2010 | Habermeyer et al. |
| 7,678,150 B2 | 3/2010 | Tornier et al. |
| 7,717,956 B2 | 5/2010 | Lang |
| 7,747,305 B2 | 6/2010 | Dean et al. |
| 7,796,791 B2 | 9/2010 | Tsougarakis et al. |
| 7,799,077 B2 | 9/2010 | Lang et al. |
| 7,802,503 B2 | 9/2010 | Couvillion et al. |
| 7,822,588 B2 | 10/2010 | Mueller et al. |
| 7,831,079 B2 | 11/2010 | Kunz et al. |
| 7,927,338 B2 | 4/2011 | Laffargue et al. |
| 7,981,158 B2 | 7/2011 | Fitz et al. |
| 7,983,777 B2 | 7/2011 | Melton et al. |
| 8,007,448 B2 | 8/2011 | Barrera |
| 8,014,984 B2 | 9/2011 | Iannotti et al. |
| 8,055,487 B2 | 11/2011 | James |
| 8,062,302 B2 | 11/2011 | Lang et al. |
| 8,066,708 B2 | 11/2011 | Lang et al. |
| 8,077,950 B2 | 12/2011 | Tsougarakis et al. |
| 8,083,745 B2 | 12/2011 | Lang et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,160,325 B2 | 4/2012 | Zug et al. |
| 8,160,345 B2 | 4/2012 | Pavlovskaia et al. |
| 8,175,683 B2 | 5/2012 | Roose |
| 8,214,016 B2 | 7/2012 | Lavallee et al. |
| 8,221,430 B2 | 7/2012 | Park et al. |
| 8,231,634 B2 | 7/2012 | Mahfouz et al. |
| 8,234,097 B2 | 7/2012 | Steines et al. |
| 8,337,501 B2 | 12/2012 | Fitz et al. |
| 8,337,503 B2 | 12/2012 | Lian |
| 8,337,507 B2 | 12/2012 | Lang et al. |
| 8,343,218 B2 | 1/2013 | Lang et al. |
| 8,350,186 B2 | 1/2013 | Jones et al. |
| 8,366,771 B2 | 2/2013 | Burdulis, Jr. et al. |
| 8,377,073 B2 | 2/2013 | Wasielewski |
| 8,377,129 B2 | 2/2013 | Fitz et al. |
| 8,382,765 B2 | 2/2013 | Axelson et al. |
| 8,439,926 B2 | 5/2013 | Bojarski et al. |
| 8,444,651 B2 | 5/2013 | Kunz et al. |
| 8,457,930 B2 | 6/2013 | Schroeder |
| 8,460,304 B2 | 6/2013 | Fitz et al. |
| 8,475,463 B2 | 7/2013 | Lian |
| 8,480,753 B2 | 7/2013 | Collazo et al. |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski et al. |
| 8,532,806 B1 | 9/2013 | Masson |
| 8,532,807 B2 | 9/2013 | Metzger |
| 8,535,319 B2 | 9/2013 | Ball |
| 8,545,509 B2 | 10/2013 | Park et al. |
| 8,545,569 B2 | 10/2013 | Fitz et al. |
| 8,551,099 B2 | 10/2013 | Lang et al. |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,585,708 B2 | 11/2013 | Fitz et al. |
| 8,608,749 B2 | 12/2013 | Meridew et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,634,618 B2 | 1/2014 | Zug et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,663,333 B2 | 3/2014 | Metcalfe et al. |
| 8,682,052 B2 | 3/2014 | Fitz et al. |
| 8,690,945 B2 | 4/2014 | Fitz et al. |
| 8,709,089 B2 | 4/2014 | Lang et al. |
| 8,731,885 B2 | 5/2014 | Iannotti et al. |
| 8,734,455 B2 | 5/2014 | Park et al. |
| 8,735,773 B2 | 5/2014 | Lang |
| 8,744,148 B2 | 6/2014 | Nord et al. |
| 8,764,836 B2 | 7/2014 | De Wilde et al. |
| 8,768,028 B2 | 7/2014 | Lang et al. |
| 8,771,365 B2 | 7/2014 | Bojarski et al. |
| 8,774,900 B2 | 7/2014 | Buly et al. |
| 8,775,133 B2 | 7/2014 | Schroeder |
| 8,777,875 B2 | 7/2014 | Park |
| 8,801,719 B2 | 8/2014 | Park et al. |
| 8,808,302 B2 | 8/2014 | Roose et al. |
| 8,814,942 B2 | 8/2014 | Anthony et al. |
| 8,830,233 B2 | 9/2014 | Friedland et al. |
| 8,843,229 B2 | 9/2014 | Vanasse et al. |
| 8,864,769 B2 | 10/2014 | Stone et al. |
| 8,864,834 B2 | 10/2014 | Boileau et al. |
| 8,882,847 B2 | 11/2014 | Burdulis, Jr. et al. |
| 8,884,618 B2 | 11/2014 | Mahfouz |
| 8,888,855 B2 | 11/2014 | Roche et al. |
| 8,898,043 B2 | 11/2014 | Ashby et al. |
| 8,903,530 B2 | 12/2014 | Metzger |
| 8,906,107 B2 | 12/2014 | Bojarski et al. |
| 8,926,706 B2 | 1/2015 | Bojarski et al. |
| 8,932,361 B2 | 1/2015 | Tornier et al. |
| 8,932,363 B2 | 1/2015 | Tsougarakis et al. |
| 8,934,961 B2 | 1/2015 | Lakin et al. |
| 8,945,230 B2 | 2/2015 | Lang et al. |
| 8,951,259 B2 | 2/2015 | Fitz et al. |
| 8,951,260 B2 | 2/2015 | Lang et al. |
| 8,965,088 B2 | 2/2015 | Tsougarakis et al. |
| 8,971,606 B2 | 3/2015 | Chaoui |
| 8,974,539 B2 | 3/2015 | Bojarski et al. |
| 8,984,731 B2 | 3/2015 | Broeck et al. |

(56) References Cited

U.S. PATENT DOCUMENTS

| | | |
|---|---|---|
| 8,986,309 B1 | 3/2015 | Murphy |
| 8,989,460 B2 | 3/2015 | Mahfouz |
| 8,990,052 B2 | 3/2015 | Lavallee et al. |
| 8,992,533 B2 | 3/2015 | Blain et al. |
| 8,992,538 B2 | 3/2015 | Keefer |
| 8,998,915 B2 | 4/2015 | Fitz et al. |
| 9,011,456 B2 | 4/2015 | Ranawat et al. |
| 9,020,788 B2 | 4/2015 | Lang |
| 9,023,050 B2 | 5/2015 | Lang et al. |
| 9,055,953 B2 | 6/2015 | Lang et al. |
| 9,060,788 B2 | 6/2015 | Bollinger |
| 9,066,728 B2 | 6/2015 | Burdulis, Jr. et al. |
| 9,066,806 B2 | 6/2015 | Phipps |
| 9,072,531 B2 | 7/2015 | Fitz et al. |
| 9,084,617 B2 | 7/2015 | Lang et al. |
| 9,095,353 B2 | 8/2015 | Burdulis, Jr. et al. |
| 9,095,375 B2 | 8/2015 | Haimerl et al. |
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,126,673 B1 | 9/2015 | Green et al. |
| 9,138,258 B2 | 9/2015 | Geebelen |
| 9,180,015 B2 | 11/2015 | Fitz et al. |
| 9,186,161 B2 | 11/2015 | Lang et al. |
| 9,186,254 B2 | 11/2015 | Fitz et al. |
| 9,198,732 B2 | 12/2015 | Iannotti et al. |
| 9,204,977 B2 | 12/2015 | Bollinger |
| 9,211,199 B2 | 12/2015 | Ratron |
| 9,216,025 B2 | 12/2015 | Fitz et al. |
| 9,220,516 B2 | 12/2015 | Lang et al. |
| 9,220,517 B2 | 12/2015 | Lang et al. |
| 9,232,955 B2 | 1/2016 | Bonin, Jr. et al. |
| 9,237,950 B2 | 1/2016 | Hensley et al. |
| 9,241,724 B2 | 1/2016 | Lang et al. |
| 9,241,725 B2 | 1/2016 | Lang et al. |
| 9,278,413 B2 | 3/2016 | Sperling |
| 9,289,221 B2 | 3/2016 | Gelaude et al. |
| 9,295,481 B2 | 3/2016 | Fitz et al. |
| 9,295,482 B2 | 3/2016 | Fitz et al. |
| 9,301,768 B2 | 4/2016 | Buza et al. |
| 9,301,812 B2 | 4/2016 | Kehres et al. |
| 9,308,005 B2 | 4/2016 | Fitz et al. |
| 9,308,053 B2 | 4/2016 | Bojarski et al. |
| 9,308,091 B2 | 4/2016 | Lang |
| 9,314,256 B2 | 4/2016 | Fitz et al. |
| 9,320,608 B2 | 4/2016 | Sperling |
| 9,320,620 B2 | 4/2016 | Bojarski et al. |
| 9,326,780 B2 | 5/2016 | Wong et al. |
| 9,326,862 B2 | 5/2016 | Smith et al. |
| 9,333,085 B2 | 5/2016 | Fitz et al. |
| 9,345,548 B2 | 5/2016 | Schoenefeld et al. |
| 9,351,743 B2 | 5/2016 | Kehres et al. |
| 9,358,018 B2 | 6/2016 | Fitz et al. |
| 9,381,025 B2 | 7/2016 | Fitz et al. |
| 9,381,026 B2 | 7/2016 | Trouilloud et al. |
| 9,386,994 B2 | 7/2016 | Agnihotri et al. |
| 9,387,083 B2 | 7/2016 | Al Hares et al. |
| 9,402,726 B2 | 8/2016 | Linderman et al. |
| 9,408,615 B2 | 8/2016 | Fitz et al. |
| 9,408,616 B2 | 8/2016 | Kehres et al. |
| 9,408,686 B1 | 8/2016 | Miller et al. |
| 9,408,698 B2 | 8/2016 | Miles et al. |
| 9,414,928 B2 | 8/2016 | Sperling |
| 9,421,021 B2 | 8/2016 | Keppler |
| 9,439,767 B2 | 9/2016 | Bojarski et al. |
| 9,451,973 B2 | 9/2016 | Heilman et al. |
| 9,486,226 B2 | 11/2016 | Chao |
| 9,495,483 B2 | 11/2016 | Steines et al. |
| 9,498,233 B2 | 11/2016 | Eash |
| 9,498,344 B2 | 11/2016 | Hodorek et al. |
| 9,504,579 B2 | 11/2016 | Mahfouz et al. |
| 9,517,134 B2 | 12/2016 | Lang |
| 9,539,013 B2 | 1/2017 | Katrana et al. |
| 9,554,910 B2 | 1/2017 | Vanasse et al. |
| 9,575,931 B2 | 2/2017 | Ratron |
| 9,579,106 B2 | 2/2017 | Lo et al. |
| 9,579,110 B2 | 2/2017 | Bojarski et al. |
| 9,592,128 B2 | 3/2017 | Phipps |
| 9,597,201 B2 | 3/2017 | Bollinger |
| 9,603,711 B2 | 3/2017 | Bojarski et al. |
| 9,615,834 B2 | 4/2017 | Agnihotri et al. |
| 9,615,840 B2 | 4/2017 | Iannotti et al. |
| 9,636,229 B2 | 5/2017 | Lang et al. |
| 9,646,113 B2 | 5/2017 | Park et al. |
| 9,649,170 B2 | 5/2017 | Park et al. |
| 9,662,214 B2 | 5/2017 | Li et al. |
| 9,668,873 B2 | 6/2017 | Winslow et al. |
| 9,675,461 B2 | 6/2017 | Mahfouz |
| 9,675,471 B2 | 6/2017 | Bojarski et al. |
| 9,681,956 B2 | 6/2017 | Al Hares et al. |
| 9,684,768 B2 | 6/2017 | Lavallee et al. |
| 9,687,945 B2 | 6/2017 | Steines et al. |
| 9,693,785 B2 | 7/2017 | Theiss et al. |
| 9,700,420 B2 | 7/2017 | Fitz et al. |
| 9,700,971 B2 | 7/2017 | Lang |
| 9,713,533 B2 | 7/2017 | Taylor et al. |
| 9,713,539 B2 | 7/2017 | Haimerl et al. |
| 9,715,563 B1 | 7/2017 | Schroeder |
| 9,717,508 B2 | 8/2017 | Iannotti et al. |
| 9,737,367 B2 | 8/2017 | Steines et al. |
| 9,741,263 B2 | 8/2017 | Iannotti et al. |
| 9,757,238 B2 | 9/2017 | Metzger |
| 9,763,682 B2 | 9/2017 | Bettenga |
| 9,770,335 B2 | 9/2017 | Sperling |
| 9,775,680 B2 | 10/2017 | Bojarski et al. |
| 9,795,393 B2 | 10/2017 | Hughes et al. |
| 9,808,261 B2 | 11/2017 | Gelaude et al. |
| 9,814,533 B2 | 11/2017 | Park et al. |
| 9,820,868 B2 | 11/2017 | Witt et al. |
| 9,839,438 B2 | 12/2017 | Eash |
| 9,849,019 B2 | 12/2017 | Miller et al. |
| 9,872,773 B2 | 1/2018 | Lang et al. |
| 9,877,790 B2 | 1/2018 | Bojarski et al. |
| 9,895,230 B2 | 2/2018 | Mahfouz |
| 9,913,691 B2 | 3/2018 | Brooks |
| 9,913,723 B2 | 3/2018 | Fitz et al. |
| 9,925,048 B2 | 3/2018 | Winslow et al. |
| 9,936,962 B2 | 4/2018 | Heilman et al. |
| 9,937,046 B2 | 4/2018 | Mahfouz |
| 9,943,370 B2 | 4/2018 | Asseln et al. |
| 9,956,047 B2 | 5/2018 | Bojarski et al. |
| 9,956,048 B2 | 5/2018 | Bojarski et al. |
| 9,987,024 B2 | 6/2018 | Frey et al. |
| 9,993,341 B2 | 6/2018 | Vanasse et al. |
| 10,010,334 B2 | 7/2018 | Keppler |
| 10,010,431 B2 | 7/2018 | Eraly et al. |
| 10,019,551 B2 | 7/2018 | Zellner et al. |
| 10,085,839 B2 | 10/2018 | Wong et al. |
| 10,433,969 B2 | 10/2019 | Humphrey |
| 10,537,390 B2 | 1/2020 | Varadarajan et al. |
| 10,548,737 B2 | 2/2020 | Hodorek et al. |
| 10,722,310 B2 | 7/2020 | Luby |
| 10,736,697 B2 | 8/2020 | Chaoui et al. |
| 10,762,623 B2 | 9/2020 | Geebelen et al. |
| 10,842,510 B2 | 11/2020 | Heilman et al. |
| 10,842,512 B2 | 11/2020 | Bonin, Jr. et al. |
| 10,888,378 B2 | 1/2021 | Walch |
| 10,905,562 B2 | 2/2021 | Sbaiz et al. |
| 10,912,571 B2 | 2/2021 | Pavlovskaia et al. |
| 10,922,448 B2 | 2/2021 | McKinnon et al. |
| 10,925,658 B2 | 2/2021 | Hopkins |
| 10,973,535 B2 | 4/2021 | Iannotti et al. |
| 10,973,580 B2 | 4/2021 | Berend et al. |
| 11,033,335 B2 | 6/2021 | Zhang |
| 11,039,889 B2 | 6/2021 | Frey et al. |
| 11,051,830 B2 | 7/2021 | Jaramaz et al. |
| 11,071,592 B2 | 7/2021 | McGuan et al. |
| 11,083,525 B2 | 8/2021 | Varadarajan et al. |
| 11,090,161 B2 | 8/2021 | Hodorek |
| 11,129,678 B2 | 9/2021 | Park |
| 11,134,963 B2 | 10/2021 | Buza et al. |
| 11,141,276 B2 | 10/2021 | Kehres |
| 11,166,733 B2 | 11/2021 | Neichel et al. |

(56) References Cited

U.S. PATENT DOCUMENTS

| | | |
|---|---|---|
| 11,166,764 B2 | 11/2021 | Roh et al. |
| 11,179,249 B2 | 11/2021 | Deransart et al. |
| 11,185,417 B2 | 11/2021 | Boileau et al. |
| 11,202,675 B2 | 12/2021 | Uhde et al. |
| 11,213,305 B2 | 1/2022 | Iannotti et al. |
| 11,234,721 B2 | 2/2022 | Gargac et al. |
| 11,253,323 B2 | 2/2022 | Hughes et al. |
| 11,278,299 B2 | 3/2022 | Neichel et al. |
| 11,278,413 B1 | 3/2022 | Lang |
| 11,298,118 B1 | 4/2022 | Koo |
| 11,298,140 B2 | 4/2022 | Wilkinson et al. |
| 11,298,142 B2 | 4/2022 | Park et al. |
| 11,298,188 B2 | 4/2022 | Kehres et al. |
| 11,298,189 B2 | 4/2022 | Kelman et al. |
| 11,337,762 B2 | 5/2022 | McKinnon et al. |
| 11,344,370 B2 | 5/2022 | Park et al. |
| 11,364,127 B2 | 6/2022 | Deransart et al. |
| 11,399,851 B2 | 8/2022 | Neichel et al. |
| 11,399,894 B2 | 8/2022 | Chaoui et al. |
| 11,410,769 B1 | 8/2022 | Yildirim |
| 11,419,618 B2 | 8/2022 | Kehres et al. |
| 11,419,680 B2 | 8/2022 | Kontaxis et al. |
| 11,432,931 B2 | 9/2022 | Lang |
| 11,432,934 B2 | 9/2022 | Couture et al. |
| 11,443,846 B2 | 9/2022 | Schoenefeld et al. |
| 11,471,303 B2 | 10/2022 | Christopher |
| 11,488,721 B2 | 11/2022 | Otto et al. |
| 11,490,965 B2 | 11/2022 | Bischoff et al. |
| 11,490,966 B2 | 11/2022 | Roche et al. |
| 11,559,403 B2 | 1/2023 | Kehres |
| 11,596,479 B2 | 3/2023 | McGuan et al. |
| 11,602,360 B2 | 3/2023 | Heilman et al. |
| 11,617,591 B2 | 4/2023 | Eash |
| 11,621,086 B2 | 4/2023 | Spångberg et al. |
| 11,622,818 B2 | 4/2023 | Siemionow et al. |
| 11,653,976 B2 | 5/2023 | Bonny et al. |
| 11,660,197 B1 | 5/2023 | Lang |
| 11,696,833 B2 | 7/2023 | Casey et al. |
| 11,712,302 B2 | 8/2023 | Walch |
| 11,717,412 B2 | 8/2023 | Casey et al. |
| 11,730,497 B2 | 8/2023 | Iannotti et al. |
| 11,737,883 B2 | 8/2023 | Metcalfe et al. |
| 11,751,946 B2 | 9/2023 | Gangwar et al. |
| 11,752,000 B2 | 9/2023 | Terrill |
| 11,766,268 B2 | 9/2023 | Iannotti et al. |
| 11,766,336 B2 | 9/2023 | Penninger et al. |
| 11,819,415 B2 | 11/2023 | Metcalfe et al. |
| 11,847,755 B2 | 12/2023 | Park et al. |
| 11,850,158 B2 | 12/2023 | Simoes et al. |
| 11,883,040 B2 | 1/2024 | Bonin, Jr. et al. |
| 2001/0047210 A1 | 11/2001 | Wolf |
| 2002/0007294 A1 | 1/2002 | Bradbury et al. |
| 2002/0082741 A1 | 6/2002 | Mazumder et al. |
| 2003/0028253 A1 | 2/2003 | Stone et al. |
| 2003/0074080 A1 | 4/2003 | Murray |
| 2003/0139818 A1 | 7/2003 | Rogers et al. |
| 2004/0039259 A1 | 2/2004 | Krause et al. |
| 2004/0064189 A1 | 4/2004 | Maroney et al. |
| 2004/0102866 A1 | 5/2004 | Harris et al. |
| 2004/0133276 A1 | 7/2004 | Lang et al. |
| 2004/0138754 A1 | 7/2004 | Lang et al. |
| 2004/0171924 A1 | 9/2004 | Mire et al. |
| 2004/0181144 A1 | 9/2004 | Cinquin et al. |
| 2004/0199258 A1 | 10/2004 | Macara |
| 2004/0236424 A1 | 11/2004 | Berez et al. |
| 2004/0243481 A1 | 12/2004 | Bradbury et al. |
| 2005/0049709 A1 | 3/2005 | Tornier |
| 2005/0065617 A1 | 3/2005 | Barrera et al. |
| 2005/0065628 A1 | 3/2005 | Roose |
| 2005/0087047 A1 | 4/2005 | Farrar |
| 2005/0098915 A1 | 5/2005 | Long et al. |
| 2005/0112397 A1 | 5/2005 | Rolfe et al. |
| 2005/0197814 A1 | 9/2005 | Aram |
| 2005/0216305 A1 | 9/2005 | Funderud |
| 2006/0079963 A1 | 4/2006 | Hansen |
| 2006/0095047 A1 | 5/2006 | de la Barrera |
| 2006/0136058 A1 | 6/2006 | Pietrzak |
| 2006/0161167 A1 | 7/2006 | Myers et al. |
| 2007/0089518 A1 | 4/2007 | Ericson et al. |
| 2007/0118055 A1 | 5/2007 | McCombs |
| 2007/0118243 A1 | 5/2007 | Schroeder et al. |
| 2007/0173945 A1 | 7/2007 | Wiley et al. |
| 2007/0191741 A1 | 8/2007 | Tsai et al. |
| 2007/0198022 A1 | 8/2007 | Lang et al. |
| 2007/0198094 A1 | 8/2007 | Berelsman et al. |
| 2007/0203605 A1 | 8/2007 | Melton et al. |
| 2007/0233141 A1 | 10/2007 | Park et al. |
| 2007/0244563 A1 | 10/2007 | Roche et al. |
| 2007/0249967 A1 | 10/2007 | Buly et al. |
| 2008/0014082 A1 | 1/2008 | Kunz et al. |
| 2008/0109000 A1 | 5/2008 | Maroney et al. |
| 2008/0140209 A1 | 6/2008 | Iannotti et al. |
| 2008/0183297 A1 | 7/2008 | Boileau et al. |
| 2008/0228269 A1 | 9/2008 | McLeod et al. |
| 2008/0243127 A1 | 10/2008 | Lang et al. |
| 2008/0269596 A1 | 10/2008 | Revie et al. |
| 2008/0269906 A1 | 10/2008 | Iannotti et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2009/0089034 A1 | 4/2009 | Penney et al. |
| 2009/0099662 A1 | 4/2009 | Splieth et al. |
| 2009/0216285 A1 | 8/2009 | Ek et al. |
| 2009/0226068 A1 | 9/2009 | Fitz et al. |
| 2009/0264894 A1 | 10/2009 | Wasielewski |
| 2009/0276045 A1 | 11/2009 | Lang |
| 2009/0292464 A1 | 11/2009 | Fuchs et al. |
| 2009/0318929 A1 | 12/2009 | Tornier et al. |
| 2010/0023015 A1 | 1/2010 | Park |
| 2010/0082035 A1 | 4/2010 | Keefer |
| 2010/0087927 A1 | 4/2010 | Roche et al. |
| 2010/0114326 A1 | 5/2010 | Winslow et al. |
| 2010/0160917 A1 | 6/2010 | Fitz et al. |
| 2010/0191100 A1 | 7/2010 | Anderson et al. |
| 2010/0217270 A1 | 8/2010 | Polinski et al. |
| 2010/0222781 A1 | 9/2010 | Collazo et al. |
| 2010/0292963 A1 | 11/2010 | Schroeder |
| 2010/0303313 A1 | 12/2010 | Lang et al. |
| 2010/0305573 A1 | 12/2010 | Fitz et al. |
| 2010/0305574 A1 | 12/2010 | Fitz et al. |
| 2011/0029088 A1 | 2/2011 | Rauscher et al. |
| 2011/0035013 A1 | 2/2011 | Winslow et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0118846 A1 | 5/2011 | Katrana et al. |
| 2011/0119884 A1 | 5/2011 | Ratron |
| 2011/0137427 A1 | 6/2011 | Lappin et al. |
| 2011/0152869 A1 | 6/2011 | Ek et al. |
| 2011/0166661 A1 | 7/2011 | Boileau et al. |
| 2011/0190775 A1 | 8/2011 | Ure |
| 2011/0295329 A1 | 12/2011 | Fitz et al. |
| 2011/0304332 A1 | 12/2011 | Mahfouz |
| 2012/0010711 A1 | 1/2012 | Antonyshyn et al. |
| 2012/0041446 A1 | 2/2012 | Wong et al. |
| 2012/0041564 A1 | 2/2012 | Landon |
| 2012/0078258 A1 | 3/2012 | Lo et al. |
| 2012/0101503 A1 | 4/2012 | Lang et al. |
| 2012/0116203 A1 | 5/2012 | Vancraen et al. |
| 2012/0130434 A1 | 5/2012 | Stemniski |
| 2012/0141034 A1 | 6/2012 | Iannotti et al. |
| 2012/0143267 A1* | 6/2012 | Iannotti ............. A61B 17/1746 606/86 R |
| 2012/0245647 A1 | 9/2012 | Kunz et al. |
| 2012/0253350 A1 | 10/2012 | Anthony et al. |
| 2012/0253467 A1 | 10/2012 | Frankle |
| 2012/0276509 A1 | 11/2012 | Iannotti et al. |
| 2012/0279933 A1 | 11/2012 | Hensler et al. |
| 2012/0289965 A1 | 11/2012 | Gelaude et al. |
| 2012/0290272 A1 | 11/2012 | Bryan |
| 2012/0296339 A1 | 11/2012 | Iannotti et al. |
| 2012/0303035 A1 | 11/2012 | Geebelen |
| 2013/0024580 A1 | 1/2013 | Tsai et al. |

(56) References Cited

U.S. PATENT DOCUMENTS

| | | |
|---|---|---|
| 2013/0053968 A1 | 2/2013 | Nardini et al. |
| 2013/0110116 A1 | 5/2013 | Kehres et al. |
| 2013/0110471 A1 | 5/2013 | Lang et al. |
| 2013/0114873 A1 | 5/2013 | Chaoui |
| 2013/0172898 A1 | 7/2013 | Iannotti et al. |
| 2013/0190882 A1 | 7/2013 | Humphrey |
| 2013/0204375 A1 | 8/2013 | Winslow et al. |
| 2013/0211531 A1 | 8/2013 | Steines et al. |
| 2013/0261629 A1 | 10/2013 | Anthony et al. |
| 2013/0274752 A1 | 10/2013 | Trouilloud et al. |
| 2013/0325134 A1 | 12/2013 | Viscardi et al. |
| 2013/0338673 A1 | 12/2013 | Keppler |
| 2014/0039633 A1 | 2/2014 | Roche et al. |
| 2014/0074246 A1 | 3/2014 | Huebner et al. |
| 2014/0159282 A1 | 6/2014 | Smith et al. |
| 2014/0163564 A1 | 6/2014 | Bollinger |
| 2014/0236304 A1 | 8/2014 | Hodorek et al. |
| 2014/0257304 A1 | 9/2014 | Eash |
| 2014/0257499 A1 | 9/2014 | Winslow et al. |
| 2014/0276867 A1 | 9/2014 | Kelley et al. |
| 2014/0303938 A1 | 10/2014 | Schoenefeld et al. |
| 2014/0303990 A1 | 10/2014 | Schoenefeld et al. |
| 2014/0371863 A1 | 12/2014 | Vanasse et al. |
| 2015/0045903 A1 | 2/2015 | Neal |
| 2015/0052586 A1 | 2/2015 | Mills |
| 2015/0093283 A1 | 4/2015 | Miller et al. |
| 2015/0105787 A1 | 4/2015 | Tornier et al. |
| 2015/0112348 A1 | 4/2015 | Schoenefeld et al. |
| 2015/0150688 A1 | 6/2015 | Vanasse et al. |
| 2015/0190151 A1 | 7/2015 | Budhabbatti et al. |
| 2015/0223941 A1* | 8/2015 | Lang .................. A61B 17/1778 606/87 |
| 2015/0250552 A1 | 9/2015 | Radermacher et al. |
| 2015/0250597 A1 | 9/2015 | Lang et al. |
| 2015/0250601 A1 | 9/2015 | Humphrey |
| 2015/0265411 A1 | 9/2015 | Deransart et al. |
| 2015/0320430 A1 | 11/2015 | Kehres et al. |
| 2015/0328004 A1 | 11/2015 | Mafhouz |
| 2015/0342739 A1 | 12/2015 | Mahfouz |
| 2016/0015466 A1 | 1/2016 | Park et al. |
| 2016/0030196 A1 | 2/2016 | Eraly et al. |
| 2016/0051367 A1 | 2/2016 | Gervasi et al. |
| 2016/0067049 A1 | 3/2016 | Flaherty et al. |
| 2016/0074052 A1 | 3/2016 | Keppler et al. |
| 2016/0100907 A1 | 4/2016 | Gomes |
| 2016/0120555 A1 | 5/2016 | Bonin, Jr. et al. |
| 2016/0136904 A1 | 5/2016 | Murai et al. |
| 2016/0143744 A1 | 5/2016 | Bojarski et al. |
| 2016/0143749 A1 | 5/2016 | Holovacs et al. |
| 2016/0157937 A1 | 6/2016 | Kehres et al. |
| 2016/0166392 A1 | 6/2016 | Vanasse et al. |
| 2016/0184104 A1 | 6/2016 | Sperling |
| 2016/0192951 A1 | 7/2016 | Gelaude et al. |
| 2016/0193051 A1 | 7/2016 | Budhabhatti et al. |
| 2016/0213385 A1 | 7/2016 | Iannotti et al. |
| 2016/0242933 A1 | 8/2016 | Deransart et al. |
| 2016/0256222 A1 | 9/2016 | Walch |
| 2016/0270854 A1 | 9/2016 | Chaoui et al. |
| 2016/0296285 A1 | 10/2016 | Chaoui et al. |
| 2016/0296290 A1 | 10/2016 | Furrer et al. |
| 2016/0324648 A1 | 11/2016 | Hodorek et al. |
| 2016/0331467 A1 | 11/2016 | Slamin et al. |
| 2016/0345987 A1 | 12/2016 | Guilloux et al. |
| 2016/0374697 A1 | 12/2016 | Kehres et al. |
| 2017/0000614 A1 | 1/2017 | Mahfouz |
| 2017/0000615 A1 | 1/2017 | Mahfouz |
| 2017/0007330 A1 | 1/2017 | Britton et al. |
| 2017/0027587 A1 | 2/2017 | Fraone et al. |
| 2017/0027593 A1 | 2/2017 | Bojarski et al. |
| 2017/0027702 A1 | 2/2017 | Goldstein et al. |
| 2017/0035513 A1 | 2/2017 | Mahfouz et al. |
| 2017/0056024 A1 | 3/2017 | Chao |
| 2017/0056187 A1 | 3/2017 | Humphrey et al. |
| 2017/0071748 A1 | 3/2017 | Humphrey |
| 2017/0079803 A1 | 3/2017 | Lang |
| 2017/0105841 A1 | 4/2017 | Vanasse et al. |
| 2017/0105843 A1 | 4/2017 | Britton et al. |
| 2017/0112626 A1 | 4/2017 | Miller et al. |
| 2017/0119531 A1 | 5/2017 | Bojarski et al. |
| 2017/0143499 A1 | 5/2017 | Phipps |
| 2017/0150978 A1 | 6/2017 | Iannotti et al. |
| 2017/0151058 A1 | 6/2017 | Sperling |
| 2017/0216038 A1 | 8/2017 | Lang et al. |
| 2017/0231783 A1 | 8/2017 | Lang et al. |
| 2017/0249440 A1 | 8/2017 | Lang et al. |
| 2017/0258598 A1 | 9/2017 | Radermacher et al. |
| 2017/0273795 A1 | 9/2017 | Neichel et al. |
| 2017/0273800 A1 | 9/2017 | Emerick et al. |
| 2017/0273801 A1 | 9/2017 | Hodorek |
| 2017/0281357 A1 | 10/2017 | Taylor et al. |
| 2017/0296347 A1 | 10/2017 | Chua et al. |
| 2017/0304063 A1 | 10/2017 | Hatzidakis et al. |
| 2017/0340449 A1 | 11/2017 | Deransart et al. |
| 2017/0360567 A1 | 12/2017 | Fitz et al. |
| 2017/0367766 A1 | 12/2017 | Mahfouz |
| 2017/0367828 A1 | 12/2017 | Steines et al. |
| 2017/0367834 A1 | 12/2017 | Fitz et al. |
| 2018/0014835 A1 | 1/2018 | Lo et al. |
| 2018/0028325 A1 | 2/2018 | Bojarski et al. |
| 2018/0036019 A1 | 2/2018 | Iannotti et al. |
| 2018/0161176 A1 | 6/2018 | Vivanz et al. |
| 2018/0228614 A1 | 8/2018 | Lang et al. |
| 2018/0233222 A1 | 8/2018 | Daley et al. |
| 2018/0235642 A1 | 8/2018 | Amis et al. |
| 2018/0235706 A1 | 8/2018 | Asseln et al. |
| 2018/0235762 A1 | 8/2018 | Radermacher et al. |
| 2018/0263782 A1 | 9/2018 | Lang et al. |
| 2018/0289380 A1 | 10/2018 | Mauldin et al. |
| 2018/0325526 A1 | 11/2018 | Haddad |
| 2019/0000629 A1 | 1/2019 | Winslow |
| 2019/0015113 A1 | 1/2019 | Morvan |
| 2019/0015116 A1 | 1/2019 | Neichel et al. |
| 2019/0015117 A1 | 1/2019 | Neichel et al. |
| 2019/0015118 A1 | 1/2019 | Neichel et al. |
| 2019/0015119 A1 | 1/2019 | Athwal et al. |
| 2019/0015221 A1 | 1/2019 | Neichel et al. |
| 2019/0021866 A1 | 1/2019 | Vanasse et al. |
| 2019/0029757 A1 | 1/2019 | Roh et al. |
| 2019/0038360 A1 | 2/2019 | Chaoui |
| 2019/0069913 A1 | 3/2019 | Iannotti et al. |
| 2019/0090952 A1 | 3/2019 | Bonny et al. |
| 2019/0142519 A1 | 5/2019 | Siemionow et al. |
| 2019/0175354 A1 | 6/2019 | Knox et al. |
| 2019/0201005 A1 | 7/2019 | Schoenefeld et al. |
| 2019/0269415 A1 | 9/2019 | Lo et al. |
| 2019/0365473 A1 | 12/2019 | Kehres et al. |
| 2020/0030034 A1 | 1/2020 | Kontaxis et al. |
| 2020/0078180 A1 | 3/2020 | Casey |
| 2020/0113632 A1 | 4/2020 | Varadarajan et al. |
| 2020/0155323 A1 | 5/2020 | Lang et al. |
| 2020/0170802 A1 | 6/2020 | Casey |
| 2020/0188121 A1 | 6/2020 | Boux De Casson et al. |
| 2020/0188134 A1 | 6/2020 | Mullen et al. |
| 2020/0281728 A1 | 9/2020 | Kulper et al. |
| 2020/0289276 A1 | 9/2020 | Lefebvre et al. |
| 2020/0330161 A1 | 10/2020 | Chaoui et al. |
| 2020/0405330 A1 | 12/2020 | Bonin, Jr. et al. |
| 2021/0030477 A1 | 2/2021 | Zuhars et al. |
| 2021/0045888 A1 | 2/2021 | Sbaiz et al. |
| 2021/0068844 A1 | 3/2021 | Lo et al. |
| 2021/0085475 A1 | 3/2021 | Hodorek et al. |
| 2021/0128179 A1 | 5/2021 | Dupuis et al. |
| 2021/0128244 A1 | 5/2021 | Couture et al. |
| 2021/0196290 A1 | 7/2021 | Iannotti et al. |
| 2021/0228277 A1 | 7/2021 | Chaoui et al. |
| 2021/0228371 A1 | 7/2021 | Deransart et al. |
| 2021/0228372 A1 | 7/2021 | Knox et al. |
| 2021/0259844 A1 | 8/2021 | Penninger et al. |
| 2021/0307833 A1 | 10/2021 | Farley et al. |
| 2021/0307911 A1 | 10/2021 | Metcalfe et al. |
| 2021/0315642 A1 | 10/2021 | McGuan et al. |
| 2021/0322130 A1 | 10/2021 | Penney et al. |
| 2021/0330389 A1 | 10/2021 | Varadarajan et al. |
| 2021/0338435 A1 | 11/2021 | Hodorek |

(56) References Cited

U.S. PATENT DOCUMENTS

| | | |
|---|---|---|
| 2021/0386435 A1 | 12/2021 | Buza et al. |
| 2022/0022895 A1 | 1/2022 | Neichel et al. |
| 2022/0031475 A1 | 2/2022 | Deransart et al. |
| 2022/0047278 A1 | 2/2022 | Fitz et al. |
| 2022/0054197 A1 | 2/2022 | Plessers et al. |
| 2022/0096240 A1 | 3/2022 | Neichel et al. |
| 2022/0110644 A1 | 4/2022 | Gargac et al. |
| 2022/0110685 A1 | 4/2022 | McGuan et al. |
| 2022/0125515 A1 | 4/2022 | McGuan et al. |
| 2022/0148454 A1 | 5/2022 | Jaramaz et al. |
| 2022/0160376 A1 | 5/2022 | Neichel et al. |
| 2022/0160405 A1 | 5/2022 | Casey et al. |
| 2022/0160439 A1 | 5/2022 | Ryan et al. |
| 2022/0183757 A1 | 6/2022 | Caldera et al. |
| 2022/0202497 A1 | 6/2022 | Janna et al. |
| 2022/0211507 A1 | 7/2022 | Simoes et al. |
| 2022/0249168 A1 | 8/2022 | Besier et al. |
| 2022/0257321 A1 | 8/2022 | Kehres et al. |
| 2022/0273450 A1 | 9/2022 | Steines et al. |
| 2022/0287850 A1 | 9/2022 | Daudet |
| 2022/0296259 A1 | 9/2022 | Shah |
| 2022/0313440 A1 | 10/2022 | Metcalfe et al. |
| 2022/0330957 A1 | 10/2022 | Neichel et al. |
| 2022/0338933 A1 | 10/2022 | Metcalfe et al. |
| 2022/0338998 A1 | 10/2022 | Sperling |
| 2022/0346968 A1 | 11/2022 | Pettersson et al. |
| 2022/0351828 A1 | 11/2022 | Chaoui |
| 2022/0354658 A1 | 11/2022 | Knox et al. |
| 2022/0370142 A1 | 11/2022 | Schoenefeld et al. |
| 2022/0387110 A1 | 12/2022 | Chaoui |
| 2022/0395376 A1 | 12/2022 | Poon et al. |
| 2023/0000645 A1 | 1/2023 | Christopher |
| 2023/0045575 A1 | 2/2023 | Lang et al. |
| 2023/0048940 A1 | 2/2023 | Kontaxis et al. |
| 2023/0061695 A1 | 3/2023 | Couture et al. |
| 2023/0079807 A1 | 3/2023 | Metcalfe et al. |
| 2023/0085093 A1 | 3/2023 | Chaoui et al. |
| 2023/0109478 A1 | 4/2023 | Chaoui et al. |
| 2023/0139531 A1 | 5/2023 | Roche et al. |
| 2023/0148085 A1 | 5/2023 | Paul et al. |
| 2023/0181257 A1 | 6/2023 | McGuan et al. |
| 2023/0248435 A1 | 8/2023 | Bonny et al. |
| 2023/0317298 A1 | 10/2023 | Spångberg et al. |
| 2023/0329791 A1 | 10/2023 | Chaoui et al. |
| 2023/0346397 A1 | 11/2023 | Iannotti et al. |
| 2023/0346480 A1 | 11/2023 | Walch |
| 2023/0355401 A1 | 11/2023 | Metcalfe et al. |
| 2023/0363915 A1 | 11/2023 | Metcalfe et al. |
| 2023/0372018 A1 | 11/2023 | Gangwar et al. |
| 2023/0372111 A1 | 11/2023 | Terrill |

FOREIGN PATENT DOCUMENTS

| | | | |
|---|---|---|---|
| CA | 2927811 | 4/2015 | |
| CA | 2938709 | 5/2015 | |
| CA | 3203261 A1 | 7/2022 | |
| EP | 1 249 213 | 10/2002 | |
| EP | 1 265 555 | 12/2002 | |
| EP | 1 563 810 | 8/2005 | |
| EP | 1 862 151 | 12/2007 | |
| EP | 1 902 689 | 3/2008 | |
| EP | 1 952 788 | 8/2008 | |
| EP | 2 135 576 | 12/2009 | |
| EP | 1 917 051 B1 | 6/2010 | |
| EP | 2 243 445 | 10/2010 | |
| EP | 2 324 801 A1 | 5/2011 | |
| EP | 2 501 313 | 9/2012 | |
| EP | 2 544 601 | 1/2013 | |
| EP | 2583242 | 4/2013 | |
| EP | 1858430 B1 | 10/2013 | |
| EP | 2471483 B1 | 10/2013 | |
| EP | 2670314 B1 | 8/2014 | |
| EP | 2 845 547 | 3/2015 | |
| EP | 2 965 720 | 1/2016 | |
| EP | 1323395 B1 | 8/2016 | |
| EP | 3057518 | 8/2016 | |
| EP | 3057524 | 8/2016 | |
| EP | 3065671 | 9/2016 | |
| EP | 3068317 | 9/2016 | |
| EP | 2 874 570 B1 | 1/2017 | |
| EP | 3 117 801 | 1/2017 | |
| EP | 2244654 B1 | 3/2017 | |
| EP | 2770920 B1 | 7/2017 | |
| EP | 2770919 B1 | 8/2017 | |
| EP | 2303192 B1 | 11/2018 | |
| EP | 3760142 A1 | 1/2021 | |
| EP | 3248553 B1 | 3/2021 | |
| EP | 3845154 A1 | 7/2021 | |
| EP | 3481318 B1 | 9/2022 | |
| FR | 2 579 454 | 10/1986 | |
| FR | 2 859 099 | 3/2005 | |
| FR | 2962573 A1 | 1/2012 | |
| FR | 2982694 B1 | 11/2016 | |
| FR | 2982979 B1 | 11/2016 | |
| FR | 2982693 B1 | 12/2016 | |
| GB | 2501494 A | 10/2013 | |
| JP | 3179628 U | 11/2012 | |
| WO | WO 93/025157 | 12/1993 | |
| WO | WO 00/35346 | 6/2000 | |
| WO | WO 00/59411 | 10/2000 | |
| WO | WO 02/061688 | 8/2002 | |
| WO | 2005016123 A2 | 2/2005 | |
| WO | WO-2006106419 A2 * | 10/2006 | ........... A61B 17/155 |
| WO | 2008021494 A2 | 2/2008 | |
| WO | 2008117028 A1 | 10/2008 | |
| WO | WO 2010/120346 | 10/2010 | |
| WO | WO 2011/110374 | 9/2011 | |
| WO | 2011142998 A1 | 11/2011 | |
| WO | WO 2011/154891 | 12/2011 | |
| WO | WO 2011/157961 | 12/2011 | |
| WO | WO 2012/021241 | 2/2012 | |
| WO | WO 2012/058349 | 5/2012 | |
| WO | WO 2012/125319 | 9/2012 | |
| WO | 2012141790 A1 | 10/2012 | |
| WO | 2012170376 A2 | 12/2012 | |
| WO | WO 2013/060851 | 5/2013 | |
| WO | WO 2013/062848 | 5/2013 | |
| WO | WO 2013/062851 | 5/2013 | |
| WO | WO-2013060851 A1 * | 5/2013 | ......... A61B 17/1778 |
| WO | WO 2013/142998 | 10/2013 | |
| WO | WO 2014/020561 | 2/2014 | |
| WO | WO 2014/035991 | 3/2014 | |
| WO | 2014145267 A1 | 9/2014 | |
| WO | WO 2014/180972 | 11/2014 | |
| WO | 2015018921 A1 | 2/2015 | |
| WO | WO 2015/052586 | 4/2015 | |
| WO | WO 2015/056097 | 4/2015 | |
| WO | 2015071757 A1 | 5/2015 | |
| WO | WO 2015/068035 | 5/2015 | |
| WO | WO 2015/071757 | 5/2015 | |
| WO | WO 2015/175397 | 11/2015 | |
| WO | WO 2015/185219 | 12/2015 | |
| WO | WO 2017/091657 | 6/2017 | |
| WO | WO 2017/105815 | 6/2017 | |
| WO | WO 2017/106294 | 6/2017 | |
| WO | WO 2017/184792 | 10/2017 | |
| WO | WO 2017/214537 | 12/2017 | |
| WO | WO 2018/022227 | 2/2018 | |
| WO | WO 2019/014278 | 1/2019 | |
| WO | WO 2019/014281 | 1/2019 | |
| WO | WO 2019/033037 | 2/2019 | |

OTHER PUBLICATIONS

Communication Pursuant to Article 94(3) issued in connection with European Patent Application No. 19759204.1, dated May 9, 2023, 6 pages.

Boileau, et al., "The three-dimensional geometry of the proximal humerus: implications for surgical technique and prosthetic design." The Journal of bone and joint surgery. British vol. 79.5 (1997): 857-865.

Habets, et al., Computer assistance in orthopaedic surgery. Technische Universiteit Eindhoven, 2002.

(56) References Cited

OTHER PUBLICATIONS

Hempfing, et al. "Surgical landmarks to determine humeral head retrotorsion for hemiarthroplasty in fractures." Journal of shoulder and elbow surgery 10.5 (2001): 460-463.
Ma, et al., "Robust registration for computer-integrated orthopedic surgery: laboratory validation and clinical experience." Medical image analysis 7.3 (2003): 237-250.
"Olympia Total Shoulder System Surgical Technique", Wright Medical Technology, 2001, in 19 pages.
Radermacher, K., et al., "Computer Assisted Orthopaedic Surgery with Image Based Individual Templates," Clinical Orthopaedics and Related Research, No. 354, Sep. 1998, pp. 28-38.
Radermacher, K., et al., "Image Guided Orthopedic Surgery Using Individual Templates: Experimental Results and Aspects of the Development of a Demonstrator for Pelvis Surgery", Health Care Sector, Telematics Applications Program, 1997, pp. 606-615.
Tornier, "Salto Talaris, Total Ankle Prosthesis", 2009.
Valstar, et al. "Towards computer-assisted surgery in shoulder joint replacement." ISPRS journal of photogrammetry and remote sensing 56.5-6 (2002): 326-337.
Valstar, et al. "The use of Roentgen stereophotogrammetry to study micromotion of orthopaedic implants." ISPRS journal of photogrammetry and remote sensing 56.5-6 (2002): 376-389.
Welsh, et al., "CT-based preoperative analysis of scapula morphology and glenohumeral joint geometry." Computer Aided Surgery 8.5 (2003): 264-268.
Zimmer, "Zimmer® PSI Shoulder Trabecular Metal™ Reverse Glenoid Base Plate Surgical Technique", Dec. 30, 2013.
Extended European Search Report issued in EP Application No. 18187134.4, dated Nov. 22, 2018 in 6 pages.
International Search Report and Written Opinion for PCT/IB2014/002711 dated Mar. 23, 2015 in 12 pages.
Dougherty, "Digital Image Processing for Medical Applications," May 11, 2009 (May 11, 2009), Cambridge University Press, XP002615721.
Gregory, et al.,"Accuracy of Glenoid Component Placement in Total Shoulder Arthroplasty and Its Effect on Clinical and Radiological Outcome in a Retrospective, Longitudinal, Monocentric Open Study," PLOS One, p. e75791, Aug. 1, 2013, vol. 8, No. 10.
Iannotti et al., "Prosthetic positioning in total shoulder arthroplasty," Journal of Shoulder and Elbow Surgery, Jan. 1, 2005, vol. 14, No. 1S, pp. S111-S121.
Kobashi et al., "Knowledge-Based Organ Identification from CT Images," Pattern Recognition, Elsevier, GB, vol. 28, No. 4, Apr. 1, 1995 (Apr. 1, 1995), pp. 475-491, XP004013165.
Lee, C.C. et al., "Identifying multiple abdominal organs from CT image series using a multimodule contextual neural network and spatial fuzzy rules", IEEE Transactions on Information Technology in Biomedicine, IEEE Services Center, Los Alamitos, CA, US, vol. 7, No. 3, Sep. 1, 2003 (Sep. 1, 2003) pp. 208-217, XP011100536.
Wu, et al. "An interface for the data exchange between CAS and CAD/CAM systems." International Congress Series. vol. 1256. Elsevier, 2003.
Non-Final Office Action issued in connection with U.S. Appl. No. 16/904,345, filed Feb. 15, 2022, 35 pages.
First Office Action issued in corresponding Japanese Patent Application No. 2021-506973, dated Jun. 5, 2023, 5 pages.
Non-Final Office Action issued in connection with U.S. Appl. No. 16/910,663, filed Dec. 15, 2022, 9 pages.
Non-Final Office Action issued in connection with U.S. Appl. No. 17/359,745, Nov. 26, 2023, 7 pages.
Final Office Action issued in connection with U.S. Appl. No. 16/910,663, Nov. 16, 2023, 9 pages.
Communication Pursuant to Article 94(3) issued in connection with European Patent Application No. 18746503.4, Oct. 17, 2023, 5 pages.
Non-Final Office Action issued in connection with U.S. Appl. No. 17/650,722, Nov. 15, 2023, 10 pages.
Notice of Allowance issued in connection with U.S. Appl. No. 17/645,607, Dec. 20, 2023, 11 pages.
Notice of Allowance issued in connection with U.S. Appl. No. 16/648,128, Feb. 16, 2024, 9 pages.
First Examination Report from counterpart Australian Application No. 2021201702 dated Dec. 1, 2021, 2 pp.
Marker et al., "Contour-Based Surface Reconstruction using Implicit Curve Fitting, and Distance Field Filtering and Interpolation," vol. Graphics, Jan. 2006, 9 pp.
Nguyen et al., "Design and Development of a Computer Assisted Glenoid Implantation Technique for Shoulder Replacement Surgery," Computer Aided Surgery, vol. 12, No. 3, May 2007, pp. 152-159.
First Examination Report issued in connection with corresponding Australian Patent Application No. 2019236696, Jun. 18, 2020, 4 pages.
International Search Report and Written Opinion of the International Searching Authority issued for PCT Application No. PCT/IB2014/002759 mailed Mar. 27, 2015, 13 pp.
Notice of Acceptance from counterpart Australian Application No. 2021201702 dated Apr. 1, 2022, 3 pp.
Notice of Allowance from counterpart Canadian Application No. 2,927,811 dated Jan. 18, 2022, 1 pp.
Office Action from counterpart Canadian Application No. 2,927,811, dated Apr. 29, 2021, 3 pp.
Office Action from counterpart Canadian Application No. 2,927,811, dated Nov. 17, 2020, 3 pp.
Office Action issued in connection with corresponding Canadian Patent Application No. 2,927,811, May 25, 2020, 3 pages.
Prosecution History from U.S. Appl. No. 15/029,879, dated May 17, 2018 through Dec. 16, 2020, 122 pp.
Prosecution History from U.S. Appl. No. 17/117,546, dated Dec. 10, 2020 through Mar. 14, 2023, 29 pp.
Raaijmakers et al., "A Custom-Made Guide-Wire Positioning Device for Hip Surface Replacement Arthroplasty: Description and First Results," BMC Musculoskeletal Disorders, vol. 11, Jul. 2010, 7 pp.
Response to Office Action dated Dec. 1, 2021, from counterpart Australian Application No. 2021201702 filed Mar. 30, 2022, 1 pp.
Response to Official Action from counterpart Canadian Application No. 2,927,811, dated Apr. 29, 2021, filed Aug. 26, 2021, 8 pp.
Response to Official Action from counterpart Canadian Application No. 2,927,811, dated May 25, 2020, filed Sep. 25, 2020, 19 pp.
Response to Official Action from counterpart Canadian Application No. 2,927,811, dated Nov. 17, 2020, filed Mar. 16, 2021, 15 pp.
Response to Official Action from counterpart Canadian Application No. 2,927,811, dated Oct. 10, 2019, filed Apr. 14, 2020, 11 pp.
Advisory Action from U.S. Appl. No. 16/918,347 dated Aug. 8, 2023, 2 pp.
Boissonnat, J.D., "Shape Reconstruction from Planar Cross Sections," Computer Vision, Graphics, and Image Processing, vol. 44, No. 1, Oct. 1988, 29 pp.
Communication pursuant to Article 94(3) EPC from counterpart European Application No. 19209711.1 dated Dec. 21, 2022, 4 pp.
Examination Report No. 1 from counterpart Australian Application No. 2021203700 dated Dec. 1, 2022, 5 pp.
Extended European Search Report issued in connection with corresponding European Patent Application No. 19209711.1; 12 pages, Mar. 23, 2020.
Final Office Action from U.S. Appl. No. 16/918,347 dated May 30, 2023, 18 pp.
First Examination Report from counterpart Australian Patent Application No. 2021209349 dated Oct. 6, 2022, 4 pp.
First Examination Report issued in connection with Australian Patent Application No. 2019236759 Jul. 17, 2020, 5 pages.
International Preliminary Report on Patentability from International Application No. PCT/IB2014/002819, dated Apr. 12, 2016, 12 pp.
International Search Report and Written Opinion of the International Searching Authority issued for PCT Application PCT/IB2014/002819 mailed on May 8, 2015.
Notice of Acceptance from counterpart Australian Application No. 2019236759, dated Apr. 27, 2021, 114 pp.
Notice of Acceptance from counterpart Australian Application No. 2021203700, dated Aug. 14, 2023, 41 pp.
Notice of Allowance from counterpart Canadian Application No. 2,927,086, dated Jul. 22, 2021, 1 pp.

(56) References Cited

OTHER PUBLICATIONS

Notice of Allowance from U.S. Appl. No. 16/918,347 dated Oct. 2, 2023, 2 pp.
Notice of Allowance from U.S. Appl. No. 16/918,347 dated Sep. 21, 2023, 8 pp.
Notice of Allowance from U.S. Appl. No. 17/874,452 dated Dec. 4, 2023, 5 pp.
Notice of Allowance from U.S. Appl. No. 17/874,452 dated Nov. 15, 2023, 8 pp.
Notice of Allowance from U.S. Appl. No. 17/874,472 dated Feb. 16, 2024, 18 pp.
Notice of Intent to Grant from counterpart Australian Application No. 2021209349 dated May 12, 2023, 3 pp.
Office Action from U.S. Appl. No. 16/918,347 dated Oct. 21, 2022, 19 pp.
Office Action issued in connection with Canadian Patent Application No. 2,927,086, Jan. 20, 2021, 3 pages.
Office Action issued in connection with corresponding Canadian Patent Application No. 2,927,086, Oct. 16, 2019, 7 pages.
Office Action issued in connection with European Patent Application No. 19209711.1, Dec. 22, 2020, 5 pages.
Prosecution History from Australian Patent Application No. 2014333516, dated May 6, 2016 through Oct. 31, 2019, 290 pp.
Prosecution History from European Patent Application No. 14830864.6, dated Jan. 27, 2015 through Dec. 12, 2019, 307 pp.
Prosecution History from U.S. Appl. No. 15/028,497, dated Apr. 4, 2018 through Apr. 6, 2020, 103 pp.
Prosecution History from U.S. Appl. No. 17/229,111, dated Jul. 16, 2021 through Apr. 1, 2022, 53 pp.
Response to Communication from counterpart European Application No. 19209711.1, dated Dec. 22, 2020, filed Mar. 24, 2021, 14 pp.
Response to Communication pursuant to Article 94(3) EPC dated Dec. 21, 2022, from counterpart European Application No. 19209711.1 filed Apr. 20, 2023, 25 pp.
Response to European Search Report from counterpart European Application No. 19209711.1, dated Mar. 23, 2020, filed Oct. 22, 2020, 8 pp.
Depuy, "Delta CTA Reverse Shoulder Prosthesis" Surgical Technique, Aug. 2004, 28 pages.
Boileau, et al., "Grammont Reverse Prosthesis: Design, Rationale, and Biomechanics", J. Shoulder Elbow Surg, Jan./Feb. 2005, 15 pages.
Frankle, et al., "Glenoid Morphology in Reverse Shoulder Arthroplasty: Classification and Surgical Implications", Journal of Shoulder and Elbow Surgery, 2009, 18, pp. 874-885, 12 pages.
Nguyen, et al., "Design and Development of a Computer Assisted Glenoid Implantation Technique for Shoulder Replacement Surgery", Computer Aided Surgery, May 2007; 12(3): 152-159, 8 pages.
Botha, Charl. P., "Technical Report: Devide—The Delft Visualisation and Image Processing Development Environment", May 30, 2005, 59 pages.
Botha, et al., "Pre-Operative Planning and Intra-Operative Guidance for Shoulder Replacement Surgery", Scientific Visualization: Advanced Concepts, pp. 179-195, 1998, 17 pages.
Botha, Charl. P., "Techniques and Software Architectures for Medical Visualisation and Image Processing", ASCI Dissertation Series No. 117, Sep. 12, 2005, 190 pages.
Krekel, et al., "Evaluation of Bone Impingement Prediction in Pre-Operative Planning for Shoulder Arthroplasty", Proc. IMechE. vol. 223 Part H: J. Engineering in Medicine, Oct. 14, 2008, 10 pages.
Valstar, et al. "Towards Computer-Assisted Surgery in Shoulder Joint Replacement", ISPRS Journal of Photogrammety & Remote Sensing 56 (2002) pp. 326-337, May 3, 2002, 12 pages.
Extended European Search Report issued in connection with European Patent Application No. 24162840.3, Jun. 21, 2024, 11 pages.
Non-Final Office Action issued in connection with U.S. Appl. No. 17/643,436, May 22, 2024, 13 pages.

* cited by examiner

SHOULDER PATIENT SPECIFIC INSTRUMENT

CROSS-REFERENCE TO RELATED APPLICATIONS

The present application is a divisional of U.S. application Ser. No. 16/521,466, filed on Jul. 24, 2019, which is a divisional of U.S. application Ser. No. 15/024,747, filed on Mar. 24, 2016, now U.S. Pat. No. 10,405,993, which is a national phase of PCT International Application No. PCT/IB2014/002711, filed on Nov. 11, 2014, which claims priority benefit under 35 U.S.C. § 119(e) to U.S. Provisional Application No. 61/903,814, filed on Nov. 13, 2013, both of which are incorporated by reference in their entirety herein. Any and all applications for which a foreign or domestic priority claim is identified in the Application Data Sheet as filed with the present application are hereby incorporated by reference under 37 CFR 1.57.

BACKGROUND

Field of the Invention

The present invention relates to shoulder implants. In particular, the present invention relates to glenoid implants for shoulder joints having scapula erosion and devices that facilitate implanting the same.

Description of the Related Art

In a healthy shoulder joint, the head of the humerus interacts with the glenoid cavity of the scapula to form a "ball and socket" joint. The humeral head abuts and articulates with the glenoid to provide a wide range of motion. In an unhealthy shoulder joint, the interaction between the glenoid and the humerus is compromised, requiring repair or replacement.

Replacing the glenoid articular surface of the scapula of a human with a prosthetic glenoid component is a delicate surgical operation, notably because of the muscular environment of the shoulder. It is found that, depending on the position of implantation of such a glenoid component, risks of separation of the component from the underlying scapula exist due to forces applied to this component in subsequent movements of the prosthesized shoulder. In particular, in certain patients, it was found that, even if the implantation on their scapula of such a glenoid component was perfectly centered on the articular head of the corresponding humerus on completion of the surgical implantation operation, the resumption of their activities led, more or less rapidly, to instability of the prosthesis.

Currently, several companies are working on custom devices to guide glenoid bone preparation. One example filed by Tornier, Inc. is U.S. patent application Ser. No. 12/954,423, filed 24 Nov. 2010 and published as US 2011/0130795 A1.

SUMMARY

A patient specific glenoid guide is provided to facilitate properly aligned implantation of a glenoid prosthesis into a patient. The guide shape is designed preoperatively based on the unique configuration of the scapula of the patient. The guide orientation is chosen preoperatively based on one or more of the bone structure of the patient, the wear pattern of the patient's glenoid cavity, the anchoring means of the glenoid prosthesis, or other aspects.

The guide may reversibly snap into securement with the scapula of the patient to hold the guide to the scapula during surgery. The guide may establish one or more axes through the shoulder joint about which subsequent bone preparation procedures and prosthesis implantation may be carried out. The guide may allow insertion of one or more K-wires or pins through the guide and into the scapula along the axis, and also allow removal of the guide without removing the one or more K-wires or pins.

The patient specific glenoid guide may be comprised of a central tubular element and three or more peripheral arms emanating from the central tubular element. One or more arms may terminate in a peripheral peg. One or more peripheral peg may be configured to reversibly engage with the scapula of the patient. The guide may be made by rapid prototyping or three dimensional printing methods.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4A illustrates a partial cross sectional side view of a patient specific glenoid guide.

Figure 1:
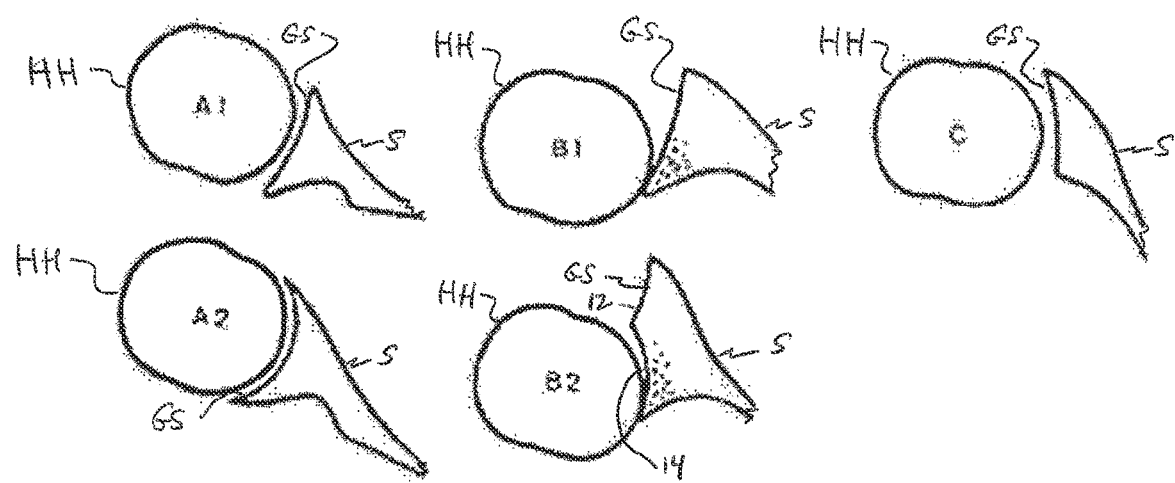
FIG. 1 illustrates schematic views of worn shoulder joints.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION OF THE PREFERRED EMBODIMENT

FIG. 1 illustrates five examples of worn shoulder joints that can be found in patients in need of shoulder arthroplasty. Each joint is comprised of a humeral head HH and a scapula S. The glenoid joint surface GS of the scapula is worn and can be classified as A1, A2, B1, B2, or C according to the shape of the glenoid surface ("Glenoid morphology in OA: Walch Classification", Walch G. et. al., J. Arthroplasty, 14:756-760, 1999). A glenoid GS may include a neo-glenoid portion 14 that has a significant amount of erosion and a paleo-glenoid portion 12 that has little or no erosion. Such a glenoid is commonly referred to as a "type-B2" glenoid (J.

Bone Joint Surg. Br. 2011 vol. 93-B no. SUPP IV, 571). A prosthetic glenoid component (not shown) can be adapted to be positioned between the scapula and the humeral component. The glenoid component is also adapted to articulate with the humeral component. The humeral component may be a humeral prosthesis secured to the humerus of the subject or an anatomical humeral head of the subject.

As part of the process for restoring a functional articular surface to the scapula a glenoid implant is firmly attached to the scapula by a fixation means (not shown). In some examples the fixation means comprises one or more screws, pegs, keels, fins, cement, or other fixation means. It is desirable to establish proper orientation of the glenoid implant in relation to the scapula and the humerus to assure that the fixation means has adequate strength to resist implant dislodgement from forces generated by articular motions of the joint. For example, screws must have adequate pull-out strength to resist articular forces of the joint that tend to dislodge the implant from the shoulder bones. Further, proper orientation of the glenoid implant in relation to the scapula and the humerus can minimize the forces generated on the glenoid implant during articulation of the shoulder joint. To facilitate proper orientation of the glenoid implant an axis through the shoulder joint can be established and the axis used to properly orient the glenoid implant so as to accomplish the above goals.

Another part of the process for properly fitting a glenoid implant to the scapula can be preparing the worn surface of the scapula so that the prepared surface will match a previously prepared surface of the glenoid implant. A surgeon may need to remove a significant amount of bone including cortical bone of the relatively healthy portions of the glenoid to accommodate typical glenoid implants. When these matched surfaces are brought into apposition the combination will resist rocking, sliding, twisting, and other articular motions of the joint that tend to dislodge the implant from the shoulder bones. To facilitate proper orientation of the glenoid implant an axis through the shoulder joint can be established and the axis used to guide scapula surface preparation tools such as reamers, guides, broaches and other devices so as to accomplish the above goals.

Figure 2:
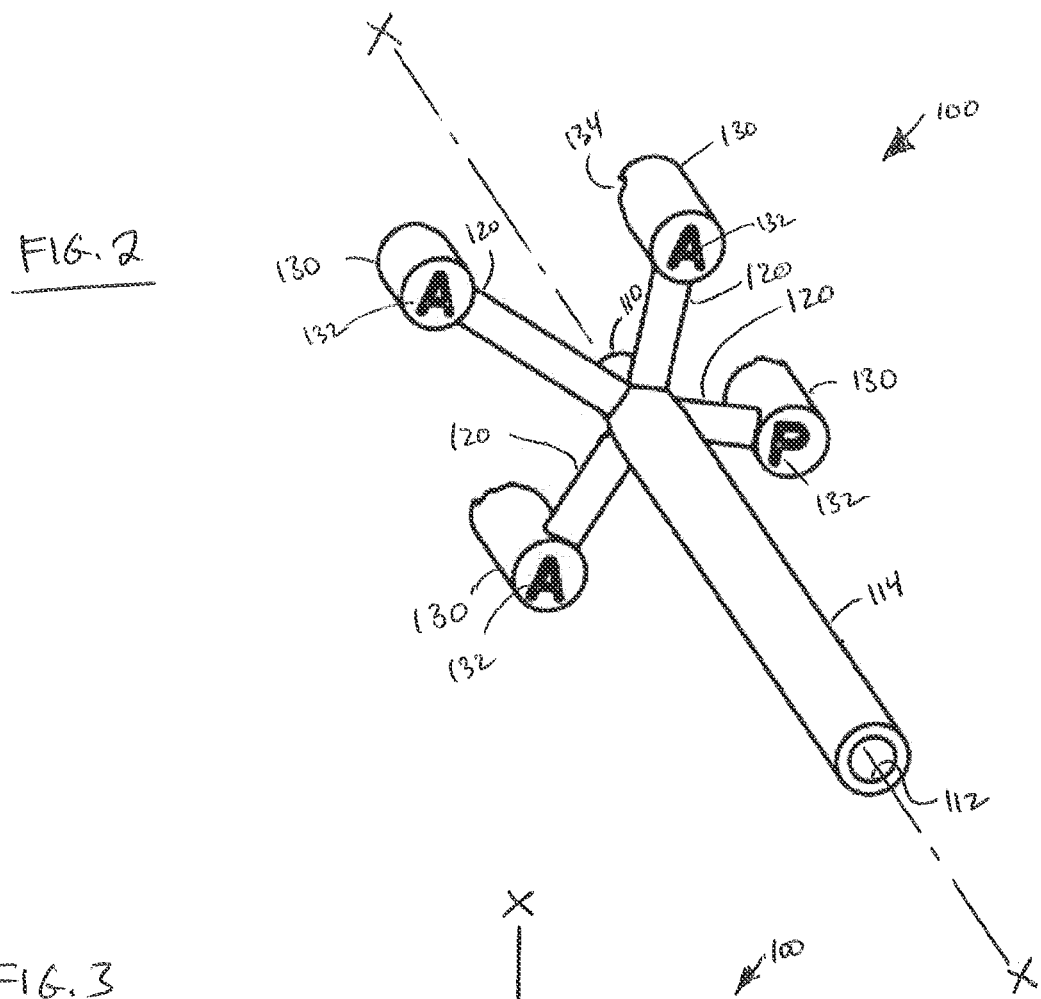
FIG. 2 illustrates an isometric plan view of a patient specific glenoid guide.
Figure 3:
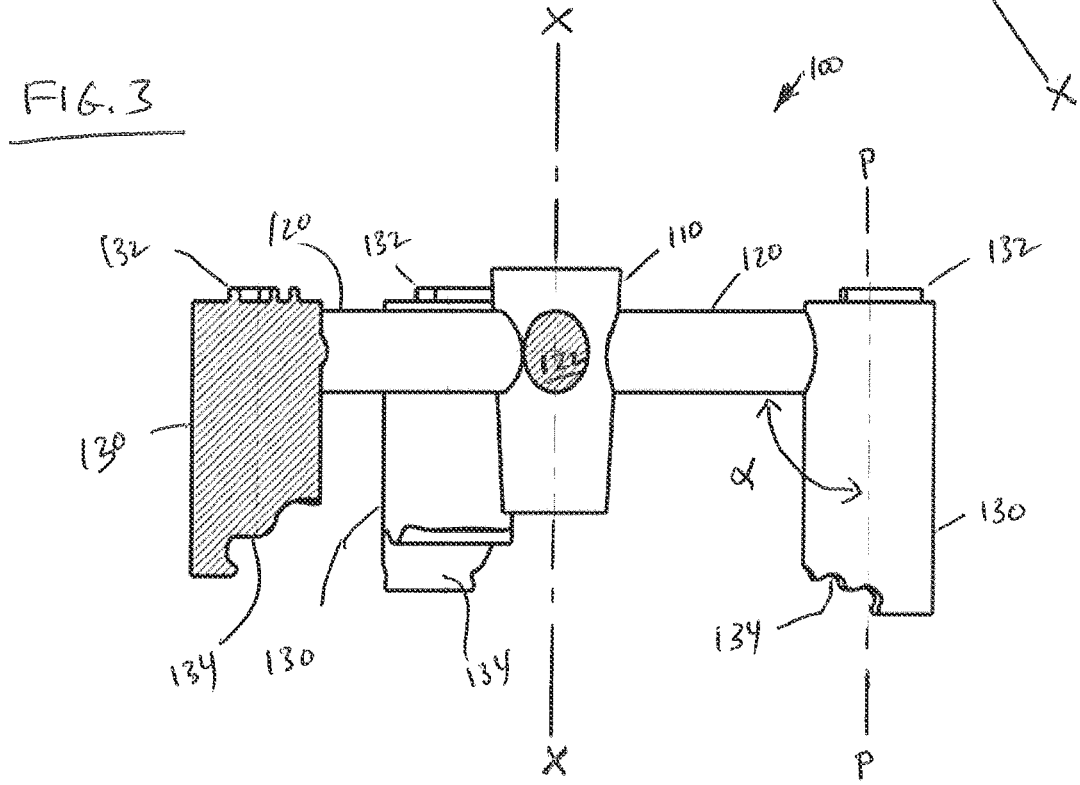
FIG. 3 illustrates a partial cross sectional side view of a patient specific glenoid guide.

FIGS. 2 and 3 illustrate one embodiment of a patient specific glenoid guide. Guide 100 is a unique structure based on the exact shoulder joint anatomy of a specific patient. Guide 100 is comprised of central tubular element 110, three or more arms 120, and at least three arms each having peripheral peg 130.

Central tubular element 110 is comprised of lumen 112 having axis X-X and is designed to guide a drill bit (not shown) for drilling a hole in the scapula. In another embodiment central tubular element 110 is designed to guide an alignment pin (not shown) through lumen 112 along axis X-X.

Figure 4B:
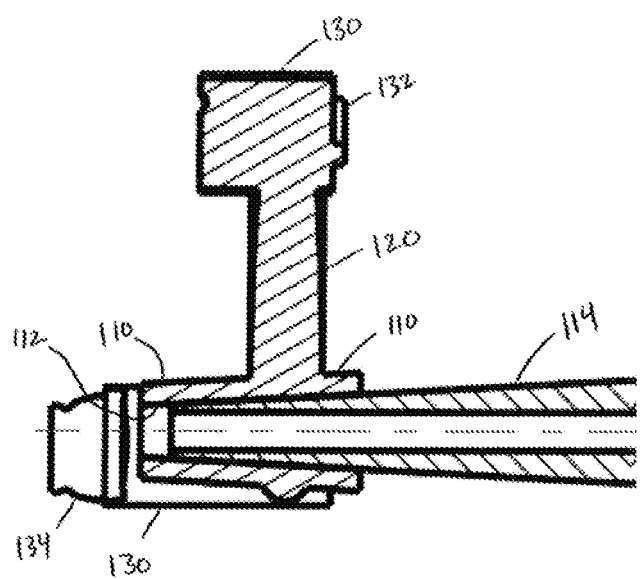
FIG. 4B illustrates a cross sectional side view of a portion of a patient specific glenoid guide.
Figure 4B:
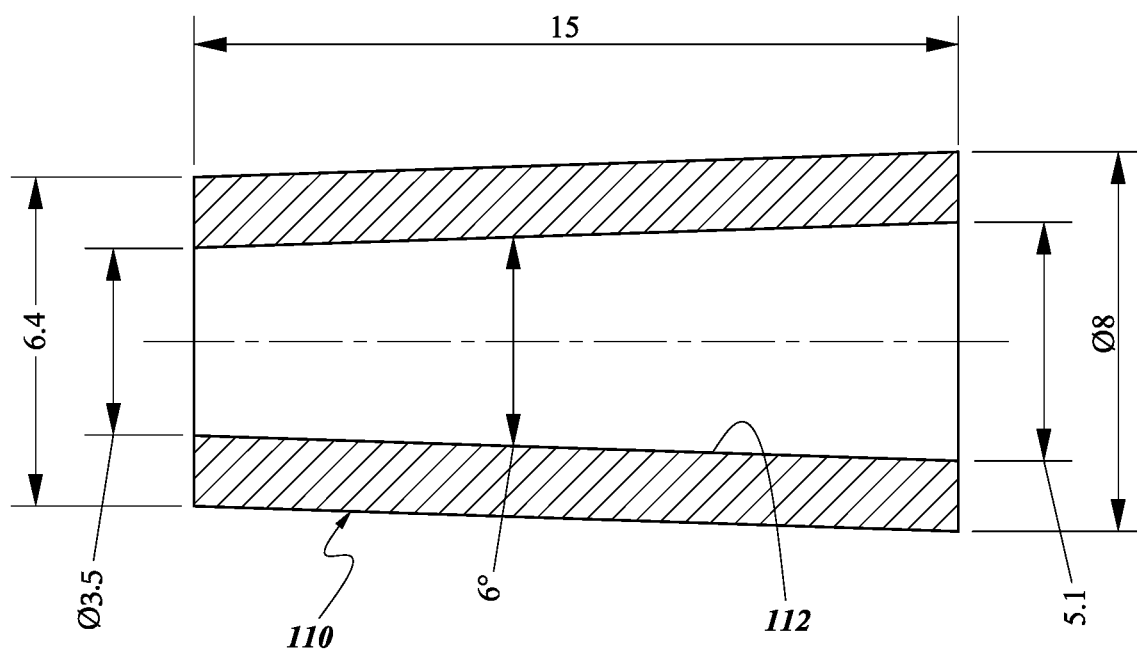

In a further embodiment (see FIGS. 4A and 4B) guide 100 is used with commercially available metallic pin guide 114 of a generic design that is not patient specific. Pin guide 114 can be engaged with lumen 112 of central tubular element 110 to hold the two components together during surgery. In one embodiment pin guide is engaged with central tubular element by friction fit. In another embodiment pin guide is engaged with central tubular element by locking conical tapers, in one example Morse tapers. Specific dimensions (in mm) of central tubular element 110 for one locking taper embodiment are illustrated in FIG. 4B, and pin guide 114 external mating dimensions are the same as the internal mating dimensions of the central tubular element. Typically pin guide 114 is long enough to function as a handle during surgery for placement of guide 100.

At least three arms 120 are provided on the guide, four arms are preferred, and 5, 6, 7, or 8 arms are contemplated. The arms between the central tubular element and each peripheral peg may have an elliptical, round, ovoid, polygonal, square, rectangular, triangular, other cross-section. In one embodiment the arm has an elliptical cross section and the major axis of the ellipse is perpendicular to the glenoid surface, the major axis is about 5 mm in length and the minor axis is about 4 mm in length. Arm 120 has a cross sectional area 122. Arm cross sectional areas of 10 square millimeters to 40 square millimeters and any cross sectional area therebetween are contemplated.

Peripheral peg 130 is comprised of identifier 132 and engagement surface 134. At least three pegs are provided on the guide, four pegs are preferred, and 5, 6, 7, or 8 pegs are contemplated. Three pegs are positioned to engage the anterior border of the glenoid cavity while one peg is positioned to engage the supero-posterior border of the glenoid cavity. Opposite to peg engagement surface 134, on the peg lateral extremity, the pegs are marked with identifier 132. In some embodiments anterior pegs are marked with identifier "A" while posterior pegs are marked with identifier "P". Peg diameters of 6 mm to 10 mm and any diameter therebetween are contemplated. In one embodiment peg diameter is 8 mm. In another embodiment the posterior peg axis P-P is angled at an obtuse angle $\alpha$ from the arm so as to not be in conflict with the posterior retractor during the arthroplasty procedure. Engagement surface 134 may be customized to closely conform to the 3 dimensional shape of the border of the glenoid cavity.

Figure 6:
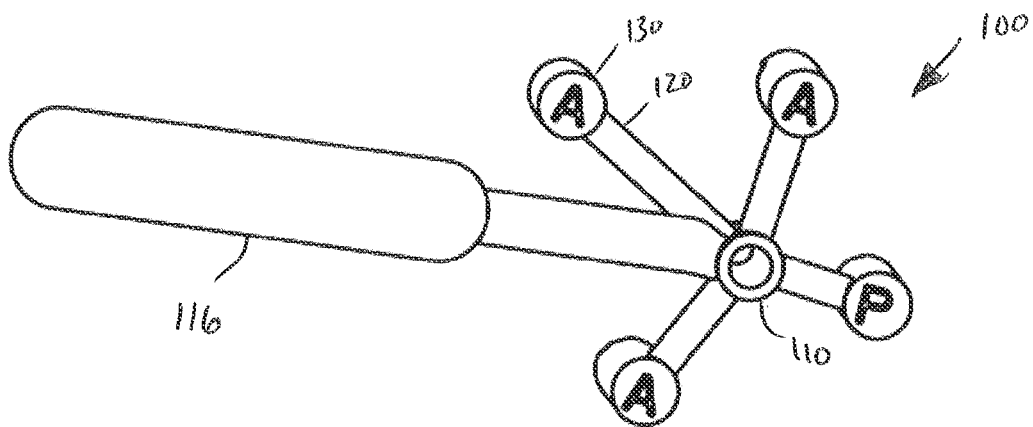
FIG. 6 illustrates an isometric plan view of an alternate embodiment of a patient specific glenoid guide.

Patient specific glenoid guide 100 optionally comprises handle 116 (FIG. 6). Handle 116 is long enough to function as a handle during surgery for placement of guide 100. Also, use of handle 116 instead of pin guide 114 for manipulation of guide 100 allows a short drill bit to be used through central tubular element 110 rather than a long drill bit through the combination of central tubular element 110 plus drill guide 114.

Figure 7:
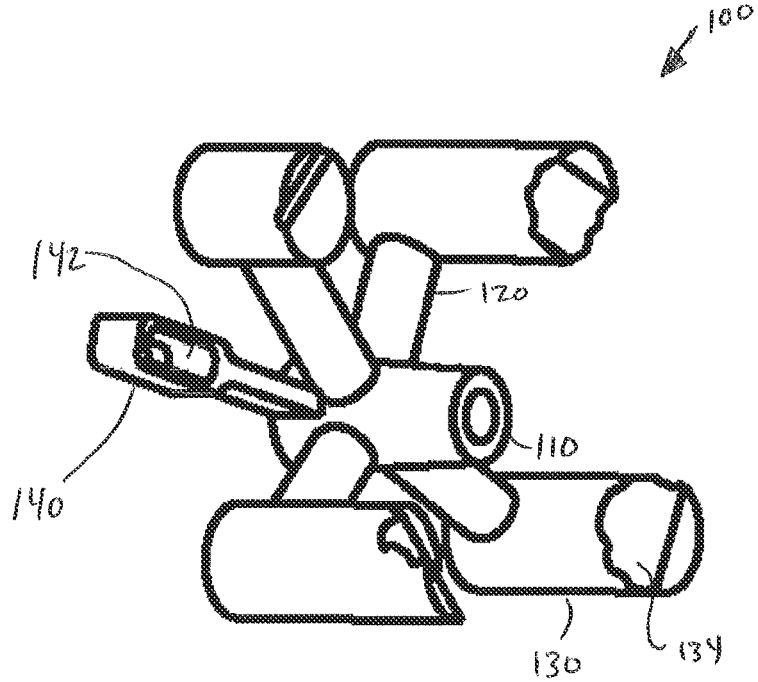
FIG. 7 illustrates an isometric bottom view of an alternate embodiment of a patient specific glenoid guide.

Patient specific glenoid guide 100 optionally comprises strut 140 having slot 142 (FIG. 7). The slot rotational position along the central axis X-X of the guide is the one of the supero-inferior axis of the glenoid component as determined by the pre-operative planning. Slot 142 is optionally used by the surgeon to mark this axis on the patient's bone with electrocautery.

In a further embodiment (not shown), second guide 100' is associated with first guide 100. Second guide 100' is similar to first guide 100 except that second guide 100' is designed to fit the patient's scapula after the scapula shape has been modified, for example, modified by reaming, and central tubular element 110' is comprised of two or more lumens 112', 112" having axes parallel to axis X-X. In some embodiment's lumens 112', 112" may be used to guide a drill bit (not shown) for drilling at least 2 holes in the scapula.

Guide 100 can be made by molding, machining, casting, thermal forming, or by other methods. In one embodiment guide 100 is made by rapid prototyping techniques, additive manufacturing or three dimensional printing using methods such as stereolithography or laser sintering. Guide 100 can be comprised of thermoplastics such as polyamide (such as PA2200 by Arptech) or metals such as titanium or stainless steel, or other materials.

Guide 100 is designed from three dimensional (3D) data about the anatomy of a patient's shoulder. The position and orientation of the axis X-X of the central tubular element 110 is defined according to pre-operative planning. The design process reproduces the translational positions of the glenoid component on three axes, (the antero-posterior axis, the supero-inferior axis and the medio-lateral axis) and it also reproduces the rotational positions of the glenoid component around the same three axes (supero-inferior axis (version), antero-posterior axis (inclination), and the medio-lateral axis (rotation)). By visualizing all of these positions a best choice position and orientation of axis X-X can be selected before operating on the patient. Also, a variety of glenoid implants can be evaluated for compatibility and performance in relation to the patients specific anatomy.

Figure 5:
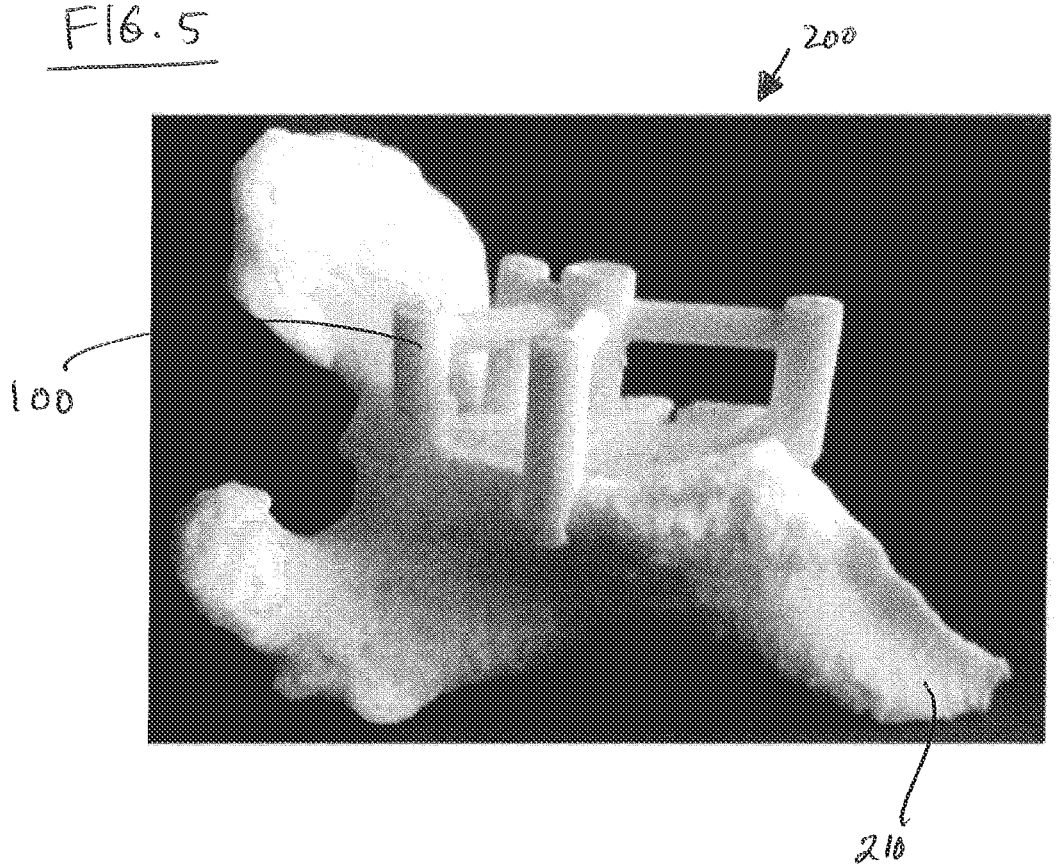
FIG. 5 illustrates an isometric plan view of a patient specific glenoid guide attached to a model of a patient's scapula.

In one exemplar embodiment a three dimensional model of the patients shoulder is generated from imaging data obtained using a medical imaging technique such as a CT scan or a MRI. The imaging data are processed manually or automatically to generate a 3D model of the patient's scapula. From the 3D model of the patient's scapula, patient-specific guide 100 is designed automatically or manually using various CAD programs and/or software available such as Solid Works or ProEngineer.

a. As a first step in this example the 3D model of the bone is displayed in a specific environment in which the surgeon is able to select the desired implant and to place it at the desired location and desired orientation in the 3D model of the patient's scapula. Alternatively the implant could be automatically selected and/or placed based on a set of pre-determined criteria such as those described in EP2324801A1 or US2011/0119884 A1 which are incorporated herein in their entirety and can be found in the Appendix.

b. As a second step in this example, once the implant is selected and placed in position in the 3D model of the patient's scapula the location of the pegs is determined by the surgeon or by an engineer. Then the guide structure, including central tubular element 110, arms 120, pegs 130, and all of their features as described above, is manually or automatically generated. A dilatation of 2 pixels of the outside dimensions of the scapula is applied to bone model, and therefore to the guide engagement surface, in order to get a proper fit between the guide and the bone model as well as between the guide and the native bone.

c. The patient-specific guide 100 so generated will have a three dimensional engagement surface at the distal end of each peg that is complementary and made to conformingly contact the anatomical surface of the glenoid cavity border. The patient-specific guide 100 is thereby configured to fit at a unique position to the anatomical surface of the scapula. The central element of the guide so generated is in the proper location and orientation for proper location of the glenoid implant.

d. Optionally a 3D bone model 210 of the patient's scapula can be produced from the 3D imaging data, and said model can be provided to the surgeon with guide 100 as part of an implant kit 200 (FIG. 5). Such a model will allow the surgeon to test the fit and orientation of the guide 100 against the model of the patient's scapula prior to surgery, and can be a reference for the surgeon during surgery.

A non-limiting exemplar method of use of the patient specific glenoid guide is now described.

a. A patient undergoes a medical imaging technique such as a CT scan or a MRI and the imaging datum are processed manually or automatically to generate a 3D model of the patient's scapula.

b. The 3D model of the scapula is displayed in a specific environment in which the surgeon selects the desired implant and places it at the desired location and desired orientation in the 3D model of the patient's scapula. Alternatively the implant is automatically selected and/or placed based on a set of pre-determined criteria such as those described in EP2324801A1 or US2011/0119884 A1 which are incorporated herein in their entirety and can be found in the Appendix.

c. The location of 4 pegs is determined by the surgeon or by an engineer.

d. The guide structure, including central tubular element 110, arms 120, pegs 130, and all of their features as described above, is manually or automatically generated. A dilatation of 2 pixels of the outside dimensions of the scapula is applied to bone model, and therefore to the guide engagement surface, in order to get a proper fit between the guide and the bone model as well as between the guide and the native bone.

e. Optionally a 3D bone model of the patient's scapula is produced from the 3D imaging data.

f. The glenoid guide is provided to the surgeon. Optionally, a kit comprised of the 3D bone model and glenoid guide is provided to the surgeon.

g. The surgeon exposes the glenoid cavity of the patient.

h. The glenoid guide is pressed onto the border of the glenoid cavity and engages the glenoid in a snap fit attachment.

i. Pin placement through lumen 112 of guide 110 into patients scapula is performed.

j. Guide 110 is removed from the pin.

k. Scapula surface preparation and/or glenoid prosthesis placement is performed using pin as a guide.

l. Pin is removed.

m. Remainder of shoulder arthroplasty procedure is completed.

Terminology

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The term "about" as used herein represent an amount close to the stated amount that still performs a desired function or achieves a desired result. For example, the term "about" may refer to an amount that is within less than 10% of the stated amount, as the context may dictate.

Any methods disclosed herein need not be performed in the order recited. The methods disclosed herein include certain actions taken by a practitioner; however, they can also include any third-party instruction of those actions, either expressly or by implication. For example, actions such as "positioning three pegs around an anterior anatomical feature adjacent of the a glenoid cavity" include "instructing the positioning of three pegs around an anterior anatomical feature adjacent of the a glenoid cavity."

Although certain embodiments and examples have been described herein, it will be understood by those skilled in the art that many aspects of the glenoid guide shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Example Embodiments

The following example embodiments identify some possible permutations of combinations of features disclosed herein, although other permutations of combinations of features are also possible.

1. A patient specific glenoid guide for attachment to a scapula of a patient, the glenoid guide comprising:
   a guide feature;
   at least three arms having a first end coupled with the guide feature and a second end disposed away from the guide feature; and
   at least three peripheral pegs, each peripheral peg extending from the second end of a corresponding arm and comprising an engagement surface;
   wherein the engagement surface is configured to engage the scapula of the patient to provide a snap fit attachment onto the scapula.

2. The patient specific glenoid guide of Embodiment 1, wherein the guide feature comprises a central tubular element that comprises a lumen.

3. The patient specific glenoid guide of Embodiment 1 or 2, wherein the guide feature is tapered.

4. The patient specific glenoid guide of any one of Embodiments 1 to 3, wherein the guide feature is configured to receive a pin guide.

5. The patient specific glenoid guide of any one of Embodiments 1 to 4, wherein the at least three peripheral pegs comprises four peripheral pegs.

6. The patient specific glenoid guide of Embodiment 5, wherein three of the four peripheral pegs are configured to engage an anterior anatomical feature of the scapula, and wherein one of the four peripheral pegs is configured to engage a supero-posterior anatomical feature of the scapula.

7. The patient specific glenoid guide of Embodiment 6, wherein three of the four peripheral pegs are configured to engage an anterior border of a glenoid cavity, and wherein one of the four peripheral pegs is configured to engage a supero-posterior border of the glenoid cavity.

8. The patient specific glenoid guide of any one of Embodiments 1 to 7, wherein each of the at least three arms comprises an elliptical cross section, the major axis of the elliptical cross-section being perpendicular to a glenoid cavity when the glenoid guide is coupled with the scapula.

9. The patient specific glenoid guide of any one of Embodiments 1 to 8, wherein an angle between one of the at least three arms and a corresponding peg is an obtuse angle.

10. The patient specific glenoid guide of any one of Embodiments 1 to 9, further comprising a lateral handle extending laterally from the guide feature.

11. The patient specific glenoid guide of any one of Embodiments 1 to 10, further comprising a strut extending laterally from the guide feature, the strut comprising a slot.

12. A system for guiding a glenoid prosthesis, the system comprising:
    the glenoid guide of any one of Embodiments 1 to 11; and
    a pin guide configured to engage the guide feature.

13. The system of Embodiment 12, wherein the pin guide comprises a tapered surface, and wherein the guide feature is tapered to receive the tapered pin guide.

14. A surgical kit comprising:
    a patient specific glenoid guide, the glenoid guide comprising:
    a guide feature;
    a plurality of arms extending from the guide feature; and
    a plurality of peripheral pegs, each of the plurality of peripheral pegs extending from a corresponding arm, each of the plurality of peripheral pegs comprising an engagement surface; and
    a three dimensional model of a patient's scapula comprising a glenoid cavity border; and
    wherein the engagement surfaces of the patient specific glenoid guide are configured to engage the glenoid cavity border of the model by a snap fit.

15. The surgical kit of Embodiment 14, wherein the guide feature comprises a central tubular element that comprises a lumen.

16. The surgical kit of Embodiment 14 or 15, wherein the guide feature is tapered.

17. The surgical kit of any one of Embodiments 14 to 16, wherein the guide feature is configured to receive a pin guide.

18. The surgical kit of any one of Embodiments 14 to 17, wherein the plurality of peripheral pegs comprises four peripheral pegs.

19. The surgical kit of Embodiment 18, wherein three of the four peripheral pegs are configured to engage an anterior portion of the glenoid cavity border, and wherein one of the four peripheral pegs is configured to engage a supero-posterior portion of the glenoid cavity border.

20. The surgical kit of any one of Embodiments 14 to 19, wherein each of the plurality of arms comprises an elliptical cross section, the major axis of the elliptical cross-section being perpendicular to a portion of the model corresponding to a glenoid cavity when the guide is applied to the model.

21. The surgical kit of any one of Embodiments 14 to 20, wherein an angle between one of the plurality of peripheral pegs and the corresponding arms is an obtuse angle.

22. The surgical kit of any one of Embodiments 14 to 21, further comprising a lateral handle extending laterally from the guide feature.

23. The surgical kit of any one of Embodiments 14 to 22, further comprising a strut extending laterally from the guide feature, the strut comprising a slot.

24. The surgical kit of any one of Embodiments 14 to 23, further comprising a pin guide coupled to the guide feature.

25. A method of guiding a glenoid prosthesis, the method comprising:
 pre-operatively determining a position and an orientation of guide feature of a glenoid guide based on a specific patient's scapula, the glenoid guide comprising:
 a plurality of arms extending from the guide feature; and
 a peripheral peg extending from each of the plurality of arms, the guide feature disposed inward of the peripheral pegs;
 engaging the glenoid guide with the scapula;
 inserting a pin having an axis through the guide feature to or through the scapula.

26. The method of Embodiment 25, wherein the guide feature comprises a central tubular element that comprises a lumen and inserting the pin comprises inserting the pin through the lumen of the guide feature.

27. The method of Embodiment 25 or 26, wherein engaging the glenoid guide with the scapula comprises engaging the glenoid guide with a glenoid cavity border by snap fit.

28. The method of any one of Embodiments 25 to 27, wherein engaging the glenoid guide with the scapula comprises positioning three pegs around an anterior anatomical feature of a glenoid cavity and positioning one peg at a supero-posterior anatomical feature of the glenoid cavity.

29. The method of Embodiment 28, wherein engaging the glenoid guide with the scapula comprises positioning three pegs around an anterior anatomical border of the glenoid cavity and positioning one peg at a supero-posterior border of the glenoid cavity.

30. The method of any one of Embodiments 25 to 29, further comprising advancing the glenoid prosthesis along the pin.

31. The method of any one of Embodiments 25 to 30, further comprising securing the pin to the guide feature by a friction fit.

32. The method of any one of Embodiments 25 to 30, further comprising securing a conical taper of the pin with a conical taper of the guide feature.

What is claimed is:

1. A method of guiding a glenoid prosthesis, the method comprising:
 pre-operatively determining a position and an orientation of a guide feature of a glenoid guide based on a scapula of a specific patient, the glenoid guide comprising:
 the guide feature that comprises a tapered lumen configured to receive a pin guide, wherein the lumen defining a central axis;
 at least four arms, each arm having a first end coupled with the guide feature and a second end disposed away from the guide feature such that each of the at least four arms extends radially outwardly from the guide feature;
 at least four peripheral pegs, each peripheral peg including a lateral end being coupled to the second end of a corresponding one of the at least four arms and comprising an engagement surface at a medial end, the engagement surface configured to engage the scapula of the patient, wherein first three peripheral pegs are positioned to engage anterior border of a glenoid cavity of the patient and fourth peg is positioned to engage supero-posterior border of the glenoid cavity; and
 a strut extending radially from the guide feature, the strut comprising a slot and positioned at a rotational position along the central axis so that the slot's rotational position along the central axis corresponds to a supero-inferior axis of the glenoid prosthesis;
 engaging the glenoid guide with the scapula such that each of the engagement surfaces contacts the border of the glenoid cavity and the at least four arms are spaced apart from a lateral surface of the glenoid; and
 inserting a pin having an axis through the tapered lumen to or through the scapula.

2. The method of claim 1, wherein the guide feature is a central tubular element that comprises the tapered lumen and inserting the pin through the guide feature comprises inserting the pin through the lumen.

3. The method of claim 1, wherein engaging the glenoid guide with the scapula comprises engaging the glenoid guide with a glenoid cavity border by snap fit.

4. The method of claim 1, wherein engaging the glenoid guide with the scapula comprises positioning the first three peripheral pegs around an anterior anatomical feature of the glenoid cavity and positioning the fourth peripheral peg at a supero-posterior anatomical feature of the glenoid cavity.

5. The method of claim 4, wherein the anterior anatomical feature of the glenoid cavity is an anterior anatomical border of the glenoid cavity and the supero-posterior anatomical feature of the glenoid cavity is a supero-posterior border of the glenoid cavity.

6. The method of claim 1, further comprising advancing the glenoid prosthesis along the pin.

7. The method of claim 1, further comprising securing the pin to the guide feature by a friction fit.

8. The method of claim 1, further comprising securing a conical taper of the pin with a conical taper of the guide feature.

9. The method of claim 1, further comprising engaging a pin guide with the tapered lumen first before inserting the pin.

10. A method of guiding a glenoid prosthesis, the method comprising:
 pre-operatively determining a position and an orientation of a guide feature of a glenoid guide based on a specific patient's scapula, the glenoid guide comprising:
 a guide feature configured to receive a pin guide;
 a plurality of arms, each arm having a first end coupled with the guide feature and a second end disposed away from the guide feature such that each arm of the plurality of arms extends radially outwardly from the guide feature; and
 a plurality of peripheral pegs, wherein each peripheral peg includes a lateral end being coupled to the second end of a corresponding one of the plurality of arms and comprising an engagement surface at a medial end, the engagement surface configured to conform to a three dimensional shape of a glenoid cavity border of the scapula of the patient, wherein the guide feature comprises a tapered lumen configured to receive the pin guide;

engaging the glenoid guide with the scapula such that each of the engagement surfaces contacts the border of the glenoid cavity and the plurality of arms are spaced apart from a lateral surface of the glenoid;

inserting a pin having an axis through the guide feature to or through the scapula.

11. The method of claim 10, wherein the guide feature is a central tubular element that comprises a tapered lumen and inserting the pin through the guide feature comprises inserting the pin through the tapered lumen.

12. The method of claim 10, wherein engaging the glenoid guide with the scapula comprises engaging the glenoid guide with a glenoid cavity border by snap fit.

13. The method of claim 10, wherein engaging the glenoid guide with the scapula comprises positioning three peripheral pegs around an anterior anatomical feature of the glenoid cavity and positioning a fourth peripheral peg at a supero-posterior anatomical feature of the glenoid cavity.

14. The method of claim 13, wherein the anterior anatomical feature of the glenoid cavity is an anterior anatomical border of the glenoid cavity and the supero-posterior anatomical feature of the glenoid cavity is a supero-posterior border of the glenoid cavity.

15. The method of claim 10, further comprising advancing the glenoid prosthesis along the pin.

16. The method of claim 10, further comprising securing the pin to the guide feature by a friction fit.

17. The method of claim 10, further comprising securing a conical taper of the pin with a conical taper of the guide feature.

* * * * *